(12) United States Patent
Kallury et al.

(10) Patent No.: US 7,056,858 B2
(45) Date of Patent: Jun. 6, 2006

(54) POLYMER WITH SUPERIOR POLAR RETENTION FOR SAMPLE PRETREATMENT

(75) Inventors: Krishna M. R. Kallury, Torrance, CA (US); David C. Jones, Long Beach, CA (US); Vipul J. Shah, West Covina, CA (US)

(73) Assignee: Varian, Inc., Palo Alto, CA (US)

( * ) Notice: Subject to any disclaimer, the term of this patent is extended or adjusted under 35 U.S.C. 154(b) by 0 days.

(21) Appl. No.: 11/154,214

(22) Filed: Jun. 16, 2005

(65) Prior Publication Data

US 2005/0277741 A1 Dec. 15, 2005

Related U.S. Application Data

(62) Division of application No. 10/252,276, filed on Sep. 23, 2002, now Pat. No. 6,926,823.

(60) Provisional application No. 60/385,604, filed on Jun. 3, 2002.

(51) Int. Cl.
*B01J 20/26* (2006.01)

(52) U.S. Cl. ..................................................... 502/402
(58) Field of Classification Search ................. 502/402
See application file for complete search history.

(56) References Cited

U.S. PATENT DOCUMENTS 6,306,959 B1 * 10/2001 Bolton et al. .............. 525/54.1

* cited by examiner

*Primary Examiner*—Robert D. Harlan
(74) *Attorney, Agent, or Firm*—Cynthia R. Moore; Bella Fishman

(57) ABSTRACT

A polymeric sorbent that can be employed in the extraction and purification of polar and nonpolar molecules from a complex media (e.g. pharmaceuticals from biological matrices) by solid phase extraction (SPE). The sorbent exhibits a strong capacity for the retention of polar molecules and can facilitate the recovery of compounds possessing a range of polarities while furnishing clean extracts showing low ion suppression. The polymer is wettable and remains wetted over long periods of time.

24 Claims, 13 Drawing Sheets

POLYMER WITH SUPERIOR POLAR RETENTION FOR SAMPLE PRETREATMENT

CROSS REFERENCE TO RELATED APPLICATIONS

The present patent application is a divisional application of the U.S. patent application Ser. No. 10/252,276, filed on Sep. 23, 2002 now U.S Pat. No. 6,926,823, which is based on and claims priority to U.S. Provisional Application Ser. No. 60/385,604, entitled "A POLYMER WITH SUPERIOR POLAR RETENTION FOR SAMPLE PRETREATMENT", which was filed Jun. 3, 2002 and is incorporated herein by reference.

FIELD OF THE INVENTION

This invention relates to a functionalized polymeric sorbent, useful for isolating an analyte of interest from an aqueous or biological matrix, through a solid phase extraction (SPE)-based sample pretreatment. The polymeric sorbent strongly retains moderately to highly polar molecules, in addition to hydrophobic compounds. The present invention also relates to a method for extraction/clean-up with this polymeric material, as well as the preparation and use of the polymeric material. The polymeric sorbent can be employed in separations and purifications in various fields, for example the pharmaceutical, diagnostic, environmental, toxicological, clinical, nutritional and agrochemical fields.

Abbreviations

ESI electrospray ionization
FTIR Fourier-transform infrared
GC gas chromatography
HPLC high performance liquid chromatography
LLE liquid-liquid extraction
LC liquid chromatography
MS mass spectrometry
NMR nuclear magnetic resonance
PS-DVB poly(styrene divinylbenzene)
SPE solid phase extraction

BACKGROUND OF THE INVENTION

Sample preparation is a critical step in the analysis of complex matrices for trace components, particularly in the area of life sciences. Solid phase extraction (SPE) techniques can be valuable to an analyst solving problems relating to sample concentration, sample clean-up and analyte isolation. SPE is recognized as a desirable alternative to liquid-liquid extraction (LLE) because SPE minimizes or eliminates altogether the use of organic solvents, which are regulated as priority pollutants. Further, LLE can lead to emulsion formation and if particulates are present in a sample, adsorption of analyte onto these structures can result in low recoveries. Compared with LLE, SPE can offer a more complete extraction of analytes, a more efficient separation of interferences from analytes, easier collection of total analyte fraction and removal of particulates and can be more easily automated. Solid phase extraction is presently extensively applied in separations performed in widely differing fields, including, but not limited to environmental pollution, agrochemicals, discovery and/or development of pharmaceuticals, analytical toxicology, the development of nutritional products, drinking water purity assessment and biotechnology. Several individual monographs, journal review articles and research publications on the theory and practice of SPE technology have been published (see, e.g., Thurman & Mills, (1998) Solid Phase Extraction, Wiley, New York, N.Y.; Simpson (Ed.), (2000) Solid Phase Extraction, Marcel Dekker, New York, N.Y.; *J. Chromatog A.* (2000) 885: entire issue; Snyder, Kirkland & Glajch, Practical HPLC Method Development Chapter 4, pp 100–173, Wiley, New York, N.Y., 1997).

Solid phase extraction protocols followed by academic, industrial and government laboratories typically employ syringe-barrel cartridges, which can include cartridges designed for syringe use, as well as disks and disk cartridges (see, e.g., Thurman & Snavely, (2000) *Trend Anal. Chem.* 19:18–26), thin packed bed syringe-barrel cartridges, solid phase microextraction fibers (for both gas chromatographic (GC) and high performance liquid chromatography (HPLC) applications), 96-well plates, SPE pipette tips, and robot-compatible large reservoirs. The syringe barrel device format is the most commonly employed format, followed by the disk format. The disk format facilitates the use of higher flow rates, due to their large cross-sectional areas and shorter bed depths, and utilize very small elution solvent volumes. For drug screening and clinical trial applications, both of which require high sample throughput and utilize liquid chromatography/mass spectrometry/mass spectrometry (LC/MS/MS) as the primary analytical tool, the multi-well plate format (e.g. 96-well plates, 384-well plates and 1536-well plates) has gained popularity.

Silica and related bonded phases constituted the dominant SPE sorbents until about 1996, as evidenced by the extensive application bibliographies prepared by several SPE material manufacturers (e.g., Varian Sample Preparation Products, Harbor City, Calif., 1995; Bakerbond SPE Bibliography, JTBaker, Inc, Philipsburg, N.J., 1995; McDonald & Bouvier, (Eds.), Solid Phase Extraction Applications Guide and Bibliography: A Resource for Sample Preparation Methods Development, Waters Corp., Milford, Mass., $6^{th}$ ed., 1995). During the last few years, however, many polymeric sorbents have been introduced for sample pretreatment applications (see, e.g., U.S. Pat. No. 5,618,438; U.S. Pat. No. 5,882,521; and U.S. Pat. No. 6,106,721; Fritz & Macka, (2000) *J. Chromatog. A* 902:137–166). Some of these polymeric sorbents are based on a styrene divinylbenzene or methacrylate polymeric backbone. Advantages of polymeric SPE sorbents over their silica-based counterparts include their stability to pH extremes and their higher surface area, which can facilitate greater capacity and retention than observed for silica-based materials. In addition, silica-based materials comprise silanol groups. These groups can complicate analyte retention, due to the influence of the pH and ionic strength of the sample matrix on the silanol groups.

One limitation of commercially available reversed-phase silica sorbents, as well as the first generation of styrene-divinylbenzene polymers, is the need for conditioning them with a wetting solvent and the additional requirement that they remain wetted prior to sample loading. The advent of second generation polymeric sorbents comprising polar functional groups such as sulfonic/carboxylic acid, hydroxymethyl, keto, nitro and heterocyclic amide moieties ameliorates these requirements due to the capacity of these polar groups to adsorb and retain water on their surface.

These reversed-phase silica and second generation polymeric materials are not, however, without problems. A major shortcoming of reversed-phase silicas and second generation polymers is the inability of these materials to retain polar compounds, such as some drug metabolites and pharmaceuticals. Many of these SPE materials exhibit unacceptable breakthrough for polar molecules during the loading and/or washing steps, resulting in poor analyte recoveries. This phenomenon places severe limitations on the applicability of SPE protocols for analyte extraction and sample clean-up when the sample comprises a mixture of an analyte, which can be hydrophobic, and its metabolites or degradation products, which tend to be very polar. Moreover, the pharmaceutical industry is designing more products with significant polar characteristics. The inadequate retention of such drugs on a polymeric sorbent during sample pretreatment can lead to serious problems.

Another limitation of prior art polymeric sorbents is in the area of ion suppression. Several publications highlight an ion suppression effect observed during LC/MS/MS analysis of drugs in biological matrices (see, e.g., Bonfiglio et al., (1999) *Rapid Commun. Mass Sp*. 13: 1175–1185; King et al., (2000) *J. Am. Soc. Mass Spectr*. 11: 942–950). These publications attribute the observed ion suppression to the presence of matrix constituents left behind on an SPE sorbent during sample loading and washing steps. These constituents can then contaminate desired extracts during analyte elution. During LC/MS, polar drugs elute from the LC column either with these matrix constituents or closely after elution of the matrix constituents. These polar drugs can be severely affected by ion suppression, rendering their quantitation unreliable. Thus, another problem associated with prior art sorbents is the presence of unacceptable levels of ion suppression.

Yet another problem associated with prior art SPE materials is the limitation on the amount of organic component that can be employed to wash (or elute) an analyte of interest after a sample comprising the analyte is applied to a prior art polymeric sorbent. Procedures for employing prior art SPE materials typically recommend the use of aqueous solvents and buffers containing a low percentage of an organic component (<5%) for washing the SPE material after a sample has been loaded onto the material. These procedures recommend a low percentage of organic component because if the organic content is increased too much, this can lead to the almost complete removal of the more polar constituents of the sample, including an analyte of interest. This is due, in part, to the inability of prior art sorbents to retain moderately to highly polar compounds. A few commercial polymeric sorbents, such as those comprising sulfonic acid moieties, are known to enhance polar retention through ionic mechanisms. SPE protocols using these sorbents are tedious, however, and such elutions are typically carried out with solvents that are incompatible with mass spectrometric detectors.

Thus, there is a need for a polymeric sorbent that strongly retains moderately to highly polar analytes, particularly when the analytes are present in a complex matrix (e.g. a biological, environmental or pharmaceutical sample). There is also a need for a polymeric sorbent that can be treated with solvents comprising a high percentage of an organic component, such that after sample loading, the sorbent can be washed thoroughly with an aqueous-organic binary solvent containing a reasonably high percentage of organic. Such a wash would furnish a clean extract by removing unwanted matrix components, which can interfere with mass spectrometric detection and cause ion suppression. An SPE protocol employing this sorbent would preferably comprise a simple procedure for elution of the desired analyte, such that the eluting solvent is compatible with mass spectrometric mode of detection and if necessary, be adapted to be injected directly into an LC/MS/MS system. Further, such a sorbent would preferably be easily solvated with an aqueous solvent (e.g. water or buffer), remain solvated for a long period of time and would display comparable SPE behavior under wet or dry conditions. Such an SPE procedure/format would preferably be compatible with the high throughput screening of large volume of samples commonly employed in the pharmaceutical industry. These and other problems are solved by the compositions and methods of present invention.

SUMMARY OF THE INVENTION

In one aspect of the present invention, a polymeric sorbent is disclosed. In one embodiment, the polymeric sorbent comprises: (a) a polymeric backbone adapted to facilitate one or more interactions selected from the group consisting of a dipolar interaction and a hydrophobic interaction; and (b) an amide functionality associated with the polymeric backbone and adapted to undergo one or more interactions selected from the group consisting of proton accepting, proton donating and dipolar interactions.

In this and other embodiments of the present invention, a polymeric backbone of a sorbent of the present invention can comprise, for example, poly(styrene divinylbenzene), copolymers of styrene, copolymers of divinylbenzene, functionalized styrenes, functionalized heterocycles and combinations thereof. An amide functionality of a sorbent of the present invention can comprise, for example, acetamide, N-alkylamides, N-aryl amides and N-heteryl amides.

In this and other embodiments of the present invention, a polymeric sorbent of the present invention can comprises between about 3.5% and about 5.0% nitrogen by mass percent and can comprise particles having a characteristic dimension (e.g. diameter) of between about 20 and about 120 microns. In another aspect, a polymeric sorbent of the present invention can remain solvated after contact with a solvent for longer than about one hour and can adsorb strongly polar, moderately polar and nonpolar molecules. In another aspect, a polymeric sorbent of the present invention, can be associated with a support, such as a cartridge, a polymeric fiber membrane, a glass fiber membrane and a multi-well plate.

In another aspect of the present invention, a method of preparing a polymeric sorbent functionalized with an amide functionality is disclosed. In one embodiment, the method comprises: (a) nitrating a polymeric backbone to form a nitrated polymeric backbone; (b) reducing the nitrated polymeric backbone to form an aminated polymeric backbone; and (c) contacting the aminated polymeric backbone with one of an acid, an acid chloride and an acid anhydride.

In one embodiment, the nitrating comprises: (a) suspending a polymeric backbone in a first solution comprising nitric acid; and (b) adding a second solution comprising a reagent adapted to generate a nitronium ion to the first solution. In one embodiment, the reducing comprises: (a) suspending a nitrated polymeric backbone in a first solution comprising a first acid; and (b) contacting the nitrated polymeric backbone with a second solution comprising a metal catalyst and a second acid. Continuing, in one embodiment, the contacting comprises: (a) suspending a reduced polymeric backbone in a first solution comprising a base to form a basic reaction solution; and (b) adding one of an acid, an acid chloride and an anhydride to the basic reaction solution. The disclosed method is not limited to the recited steps and can further comprise, for example, the steps of (a) recovering the polymeric sorbent by filtration; (b) washing the polymeric sorbent one or more times with a solution comprising an acid; (c) washing the polymeric sorbent one or more times with an aqueous solution; and (d) washing the polymeric sorbent one or more times with an organic solvent.

In yet another aspect of the present invention, a method of isolating an analyte from a sample is disclosed. In one embodiment, the method comprises: (a) conditioning the sorbent by washing the sorbent with an organic solvent followed by water; (b) contacting a sample comprising an analyte disposed in an aqueous medium with a polymeric sorbent comprising (i) a polymeric backbone adapted to form at least one of a dipolar interaction and a hydrophobic interaction; and (ii) an amide functionality associated with the backbone and adapted to undergo proton accepting and proton donating interactions; to form a sorbent-sample complex; (c) washing the sorbent-sample complex with water followed by an organic solvent; and (d) eluting an analyte from the sorbent-sample complex with an eluting solvent, whereby an analyte is isolated from a sample. A sample can be, for example, a biological matrix comprising an analyte, an environmental sample, an aqueous pharmaceutical sample or an aqueous nutraceutical sample.

DETAILED DESCRIPTION OF THE INVENTION

I. Definitions

Figure 1:
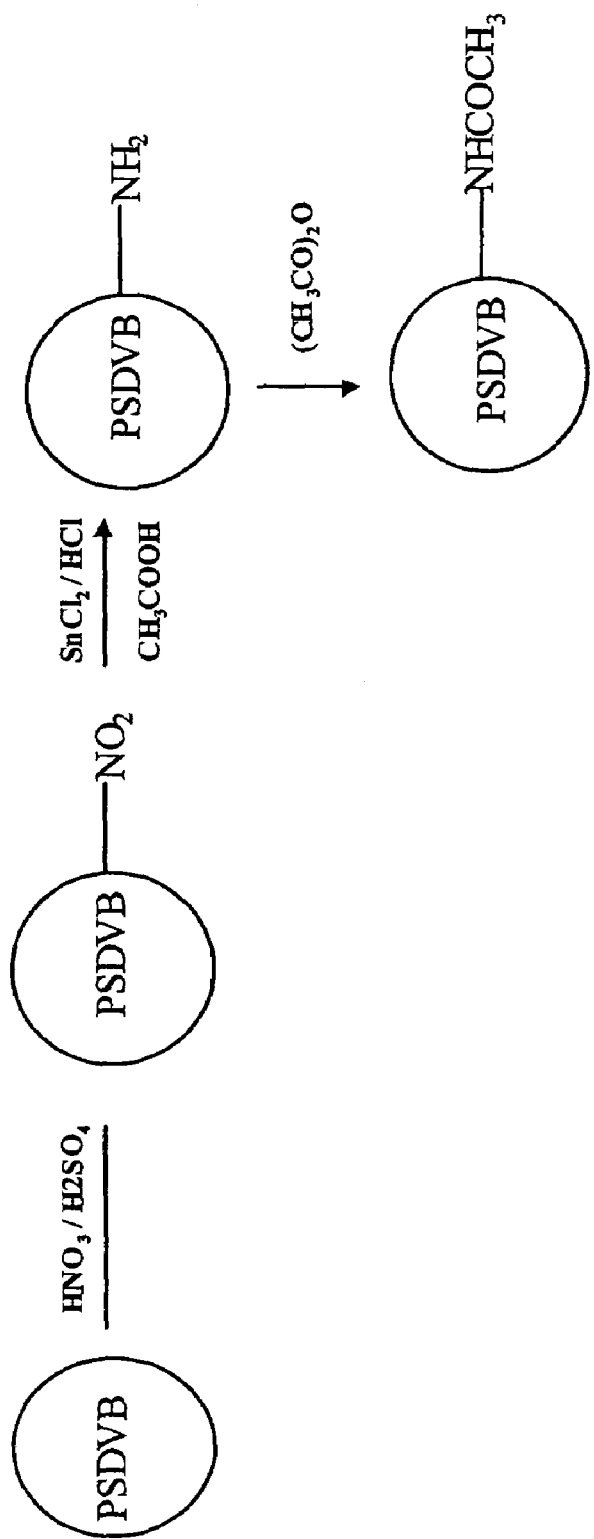
FIG. 1 is a schematic diagram generally depicting a synthetic protocol by which a polymeric sorbent of the present invention can be synthesized.

Following long-standing patent law convention, the terms "a" and "an" mean "one or more" when used in this application, including the claims.

As used herein, the term "about," when referring to a value or to an amount of mass, weight, time, volume, concentration or percentage is meant to encompass variations of ±20% or ±10%, more preferably ±5%, even more preferably ±1%, and still more preferably ±0.1% from the specified amount, as such variations are appropriate to perform the disclosed method.

As used herein, the term "adsorb", and grammatical derivatives thereof, means a surface phenomena wherein an analyte becomes reversibly associated with the surface of a polymeric sorbent by physically interacting with the surface molecules. The association can be, for example, via any non-covalent mechanism (e.g. van der Waal's forces, such as dipole-dipole interactions, dipole-induced dipole or dispersive forces, via hydrophobic interactions or hydrogen donor or acceptor interactions).

As used herein, the term "acid chloride" means a chemical entity comprising a variable organic group (R1, which can comprise hydrogen, or an alkyl, aryl or heterocyclic moiety), a carbonyl and a chlorine atom, and is represented by the chemical structure

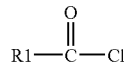

As used herein, the terms "amide," "amide group" and "amide functionality" are used interchangeably and mean a chemical entity comprising a carbonyl, a variable organic group (R1) joined to the carbonyl and a group comprising a nitrogen atom and at least two independently variable organic groups (R2 and R3, which can comprise hydrogen or an alkyl, aryl or heterocyclic moiety), and can be represented by the chemical structure

In the compositions and methods of the present invention, for example, a preferred amide is acetamide, represented by the chemical structure

wherein R1 represents a polymeric backbone. Broadly, then, the term "amide functionality" means any chemical entity comprising an amide group.

As used herein, the term "analyte" means any molecule of interest. An analyte can comprise any polarity, although in the context of the present invention, moderately polar to highly polar molecules are of particular interest. An analyte can be disposed in a sample, and can form a component thereof. For example, a candidate therapeutic compound or metabolic byproducts thereof, can be an analyte, and the analyte can be disposed in, for example, a blood plasma sample, saliva, urine, drinking water, and water known or suspected to be polluted. Summarily, an analyte can comprise any molecule of interest.

As used herein, the term "anhydride" means a chemical entity comprising two carbonyls and two variable organic groups (R1 and R2, which can comprise an alkyl, aryl or heterocyclic group), which can independently be the same or different, and can be represented by the chemical structure

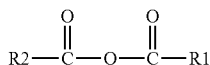

As used herein, the term "associated" means a joining of two or more chemical entities. An association can be via a covalent or via non-covalent bond (e.g., hydrophobic interaction, hydrogen bonding, ionic interactions, van der Waals' forces and dipole-dipole interactions).

As used herein, the terms "support" and "supporting format" are used interchangeably and mean a porous or non-porous water insoluble material. A support or a supporting format can have any one of a number of configurations or shapes, such as strip, plate, disk, rod, particle, including bead, and the like. A support or supporting format can be hydrophobic, hydrophilic or capable of being rendered hydrophilic, and can comprise inorganic powders such as silica, zirconia, and alumina; natural polymeric materials, synthetic or modified naturally occurring polymers, such as nitrocellulose, cellulose acetate, poly(vinyl chloride), polyacrylamide, polyacrylate, polyethylene, polypropylene, poly(4-methylbutene), polystyrene, polymethacrylate, poly(ethylene terephthalate), nylon, poly(vinyl butyrate), polytetrafluoroethylene, etc.; either used by themselves or in conjunction with other materials; glass available as Bioglass, ceramics, metals, and the like (see, e.g., Buchmeiser, (2001) *J. Chromatog. A* 918:233–266). Natural or synthetic assemblies such as liposomes, phospholipid vesicles, and cells can also be employed.

As used herein, the term "strongly polar" means a molecule that, based on the octanol-water partition coefficient log P, has a log P value of −1.0 to +0.5.

As used herein, the term "moderately polar" means a molecule that, based on the octanol-water partition coefficient log P, has a log P value of 0.5 to 1.5.

As used herein, the term "nonpolar" means a molecule that based on the octanol-water partition coefficient log P, has a log P value greater than or equal to 2.0.

II. General Considerations

An aspect of the present invention is the development of a polymeric sorbent that strongly retains moderate to highly polar molecules (e.g. pharmaceuticals, such as sulfa drugs, atenolol, ranitidine and pseudoephedrine). The retention profile of this polymer allows an analyst to load a sample onto a sorbent and subsequently subject the loaded sorbent to a very thorough wash with a binary solvent comprising an aqueous component and an organic component present, which can remove many unwanted components of the sample. Preferably the organic component (e.g. acetonitrile or methanol) is present in a high percentage (e.g. >about 10–30% organic), thereby facilitating the elimination of matrix constituents from biological or environmental samples completely and the ability to obtain purer extracts.

In the present disclosure, when referring to the polarity of a molecule (e.g. a "strongly polar" molecule, a "moderately polar" molecule, a "nonpolar" molecule, etc.), polarity is described based on the standard octanol-water partition coefficient, P. This coefficient is sometimes expressed as log P. The octanol-water partition coefficient is a measure of polarity commonly known and used by those of ordinary skill in the art. Standard methods of determining octanol-water partition coefficients are known (see, e.g., Sangster, (1997) Octanol-Water Partition Coefficients: Fundamentals and Physical Chemistry, Wiley, Hoboken N.J.) and many P values have been tabulated (see, e.g., Sangster, (1989) *J. Phys. Chem. Ref Data* 18(3):1111–1230; Howard & Meylan, (eds.) 1997 Handbook of Physical Properties of Organic Chemicals, Lewis, Boca Raton, Fla.). Specific definitions for some polarity descriptors are provided herein.

The isolation process can also minimize or eliminate any ion suppression due to interference of matrix constituents with the ionization process of analytes under investigation. The elimination of ion suppression is of benefit to operations involving electrospray ionization (ESI), for example, which is commonly employed in LC/MS/MS analyses. Additionally, since sample solutions treated by SPE protocols are predominantly aqueous in nature, solvation of the sorbent surface (commonly called wettability or hydration when water is employed) can be desirable, and can play a role in the retention of polar analytes. The polymeric sorbents of the present invention are readily solvated and can remain solvated for long periods of time (greater than about one hour).

One commercially available prior art polymeric sorbent that is extensively used in the pharmaceutical industry for sample cleanup is a copolymer comprising divinylbenzene and N-vinyl pyrrolidone. It has been stated that the introduction of the pyrrolidone component into the overall divinylbenzene-N-vinylpyrrolidone copolymeric structure provides an interactive surface for polar drugs (Bouvier et al., (1998), *LC.GC (Supplement)*, May 1998, pp S53–S58). A number of literature publications indicate, however, that when this prior art copolymer is employed in an SPE protocol, moderate to strongly polar analytes are not adequately retained and that complex pH-controlled extraction procedures are required in order to enhance the retention of moderate to strongly polar analytes on this sorbent (see, e.g., Cheng et al., (1999) *J. Chromatogr. B* 729: 19–31; Georga et al., (2001) *J. Chromatogr. B* 759: 209–218). Additionally, SPE extracts from this polymeric sorbent were found to contain impurities, presumably due to strong adsorption of matrix constituents of biological samples applied to the sorbent (see, e.g., Zheng et al., (2002) *J. Pharm. Biomed. Anal*. 28: 279–285.)

Another prior art polymeric sorbent that has been developed comprises the same divinylbenzene N-vinylpyrrolidone basic skeleton but also comprises a sulfonic acid moiety. This sorbent retains basic analytes via an ionic mechanism but, like other prior art polymeric sorbents, pH-controlled solvent systems are required to load, wash and elute basic drugs from this prior art sorbent (see, e.g., Kollroser & Schober, (2002) *J. Chromatogr. B* 766: 219–226). The purity of extracts of polar drugs from serum, obtained from this sulfonated polymer, was still found to be unacceptable, in spite of the fact that the sorbent can be subjected to strong solvent wash after the loading step (Muller et al., (2002) *J. Chromatogr. B* 773: 47–52). Further, when acidic analytes from biological matrices are to be purified, this sulfonated polymer is inefficient and an anion exchange sorbent is preferably employed.

Figure 5A:
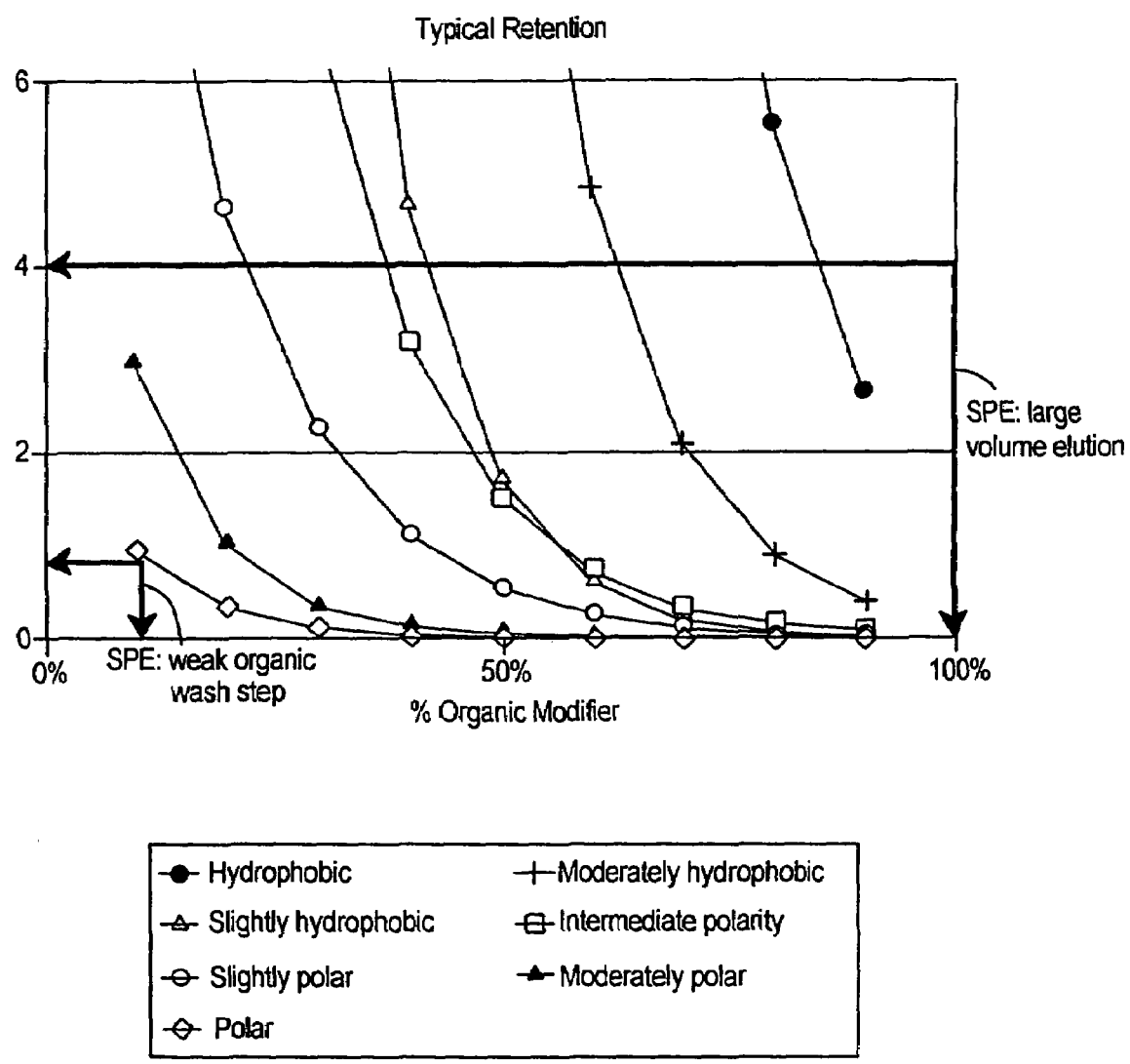
FIG. 5A is a plot depicting the typical retention profile of polar and hydrophobic compounds by prior art silica and polymer-based SPE sorbents.
Figure 5B:
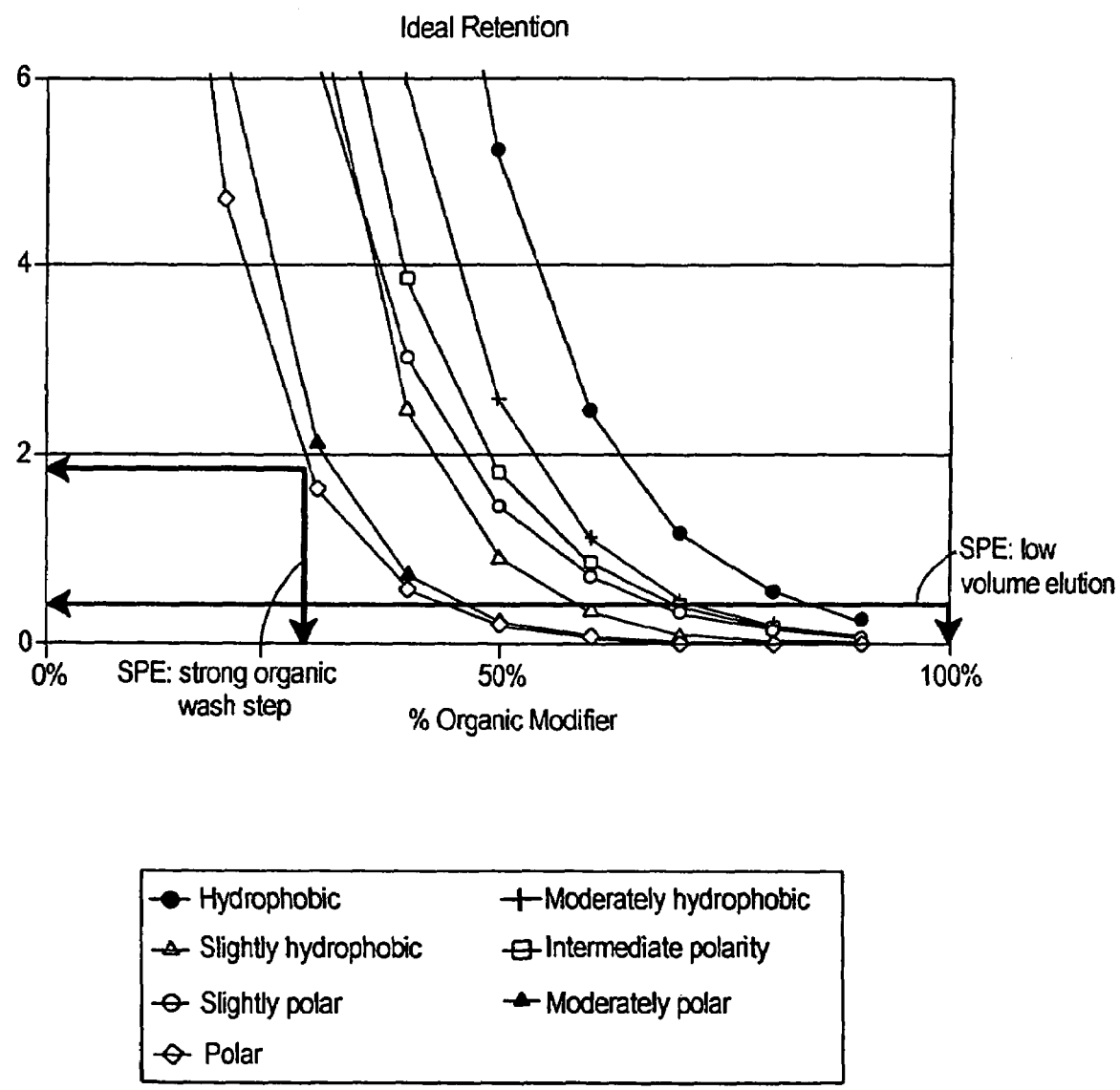
FIG. 5B is a plot depicting the preferred retention of polar and hydrophobic compounds by a sorbent during a wash step of an SPE protocol.

The retention of analytes comprising various degrees of polarity and hydrophobicity on both silica and polymer-based SPE sorbents (excluding ion-exchange resins) is presented in FIG. 5A. This figure was generated by pooling SPE data on a wide range of compounds of different polarities documented in literature, (Hennion, (1999) *J. Chromatogr. A* 856: 3–54; Casas et al., (1992) *Chromatographia* 34: 79–82; Pichon et al., (1998) *J. Chromatogr. A* 795: 83–92; Hennion et al., (1998) *J. Chromatogr. A* 823: 147–161) as well as from unpublished data recorded in the inventors' laboratories. FIG. 5A demonstrates that analytes of moderate to strong polarity show considerable breakthrough on both silica-based reversed phases and polymeric sorbents, indicating that these analytes are not retained well on these sorbents. By way of comparison, FIG. 5B depicts a preferred retention profile for polar and hydrophobic molecules. This figure depicts a hypothetical profile indicating how an ideal SPE sorbent is predicted to perform, although no state-of-the-art sorbent exhibits such an ideal behavior. In this retention profile, after a sample loading step, the sorbent is amenable to washing with an aqueous binary solvent comprising an aqueous component and an organic component comprising about 20% or more organic (e.g. acetonitrile or methanol).

Thus, commercially available prior art polymeric sorbents are unable to effectively retain moderately to highly polar analytes. Further, these sorbents are not amenable to washing with a binary solvent comprising a high percentage of an organic component, which can limit the purity of an eluted analyte. As described hereinbelow, however, the polymeric sorbents of the present invention, on the other hand, meet these criteria and can be employed to isolate moderate and highly polar analytes.

III. Theoretical Considerations for Designing A Polymeric Sorbent of the Present Invention When designing a sorbent with enhance polar retention, the solvation parameter model equation (1) can be considered.

$$\text{Log } SP = c + mV_x + rR_2 + s\pi_2^H + a\Sigma\alpha_2^H + b\Sigma\beta_2^H \quad (1)$$

wherein SP is a solute property, such as capacity factory (k') or breakthrough volume or elution volume; the solute descriptors are $V_x$, which represents molecular volume; $\pi_2^H$, which represents dipolarity/dipolarizability; and $\Sigma\alpha_2^H$ and $\Sigma\beta_2^H$, which represent a solute's effective hydrogen-bond acidity and hydrogen-bond basicity, respectively. The other parameters in the equation represent the system, which is a combination of the sorbent and the solvent. The m term is the capacity of the sorbent to form a cavity adapted to accommodate the solute. The system constant r represents the difference in the capacity of the sorbent and sample solution to interact with n or π electrons of the solute. The system constant s represents the difference in the capacity of the sorbent and sample solution to take part in dipole-dipole and dipole-induced dipole interactions. The constant denotes the difference in hydrogen-bond basicity of the sorbent and solution and the b constant denotes the difference in hydrogen-bond acidity of the sorbent and solution.

In equation (1), c is a constant, which is characteristic of the system. The two terms $mV_x$ and $rR_2$ represent the steric fit and hydrophobic interactions, respectively, between the solute and the sorbent. The other parameters, namely $s\pi_2^H$, $a\Sigma\alpha_2^H$ and $b\Sigma\beta_2^H$, represent polar interactions resulting from dipole-dipole, solute acidity-sorbent basicity and solute basicity-sorbent acidity interactions, respectively.

To enable a sorbent to interact with and retain an analyte, a sum of these interactions can be considered. For polar analytes in particular, the abovementioned polar interactions of the sorbent surface with these analytes can be of great significance with respect to analyte retention. For example, polar analytes comprise acidic and/or basic functional groups. In some cases polar analytes comprise a neutral, but strongly polar, moiety such as a glucuronide, an amide or a sulfonamide. In order to retain analytes with such functionalities, the sorbent preferably comprises hydrogen bond donor (acidic) or hydrogen bond acceptor (basic) sites in its structure. Furthermore, the strength of hydrogen bonds arising from solute-sorbent interactions are preferably higher than similar bonds a solute or sorbent can form with water or methanol, which can facilitate retention of polar analytes during a wash step of an overall sample purification and/or extraction protocol. In addition, it is preferable that a functional group meeting these goals is located on the polymeric backbone of a sorbent. It is also preferable that the polymeric backbone itself can also simultaneously undergo dipole-dipole interactions with the □ electrons of an unsaturated group or an aromatic system present on a polar analyte.

A survey of the applicable literature indicates that of the various functional classes of organic compounds, an amide functionality carrying at least one hydrogen atom on the nitrogen meets all the three criteria outlined above, namely dipole-dipole interactions, hydrogen bond basicity and hydrogen bond acidity. By way of specific example, formamide shows a π value of 0.46, a Σα value of 0.33 and a Σβ value of 0.21, while the corresponding values for N,N dimethylformamide are 0.56, 0.00 and 0.44, respectively. For N-methylpyrrolidone, the corresponding figures are 0.57, 0.00 and 0.43, respectively. The log P value of acetanilide is 1.16, while those of toluene, methyl benzoate and acetophenone are 2.74, 2.18 and 1.66, respectively. These values show that the amide functionality is the most polar amongst different classes of substituted benzenes. The hydrogen bond forming capabilities of the amide functionality is also evident from nucleic acid and protein chemistry. Thus, a polymeric sorbent adapted to retain a moderately to highly polar analyte, such as the polymeric sorbents of the present invention, preferably comprise an amide functionality.

IV. A Polymeric Sorbent of the Present Invention

A polymeric sorbent of the present invention broadly comprises a polymeric backbone adapted to facilitate one or more interactions selected from the group consisting of dipolar interactions and a hydrophobic interactions; and an amide functionality associated with the polymeric backbone and adapted to undergo one or more interactions selected from the group consisting of proton accepting, proton donating and dipolar interactions.

Figure 3A:
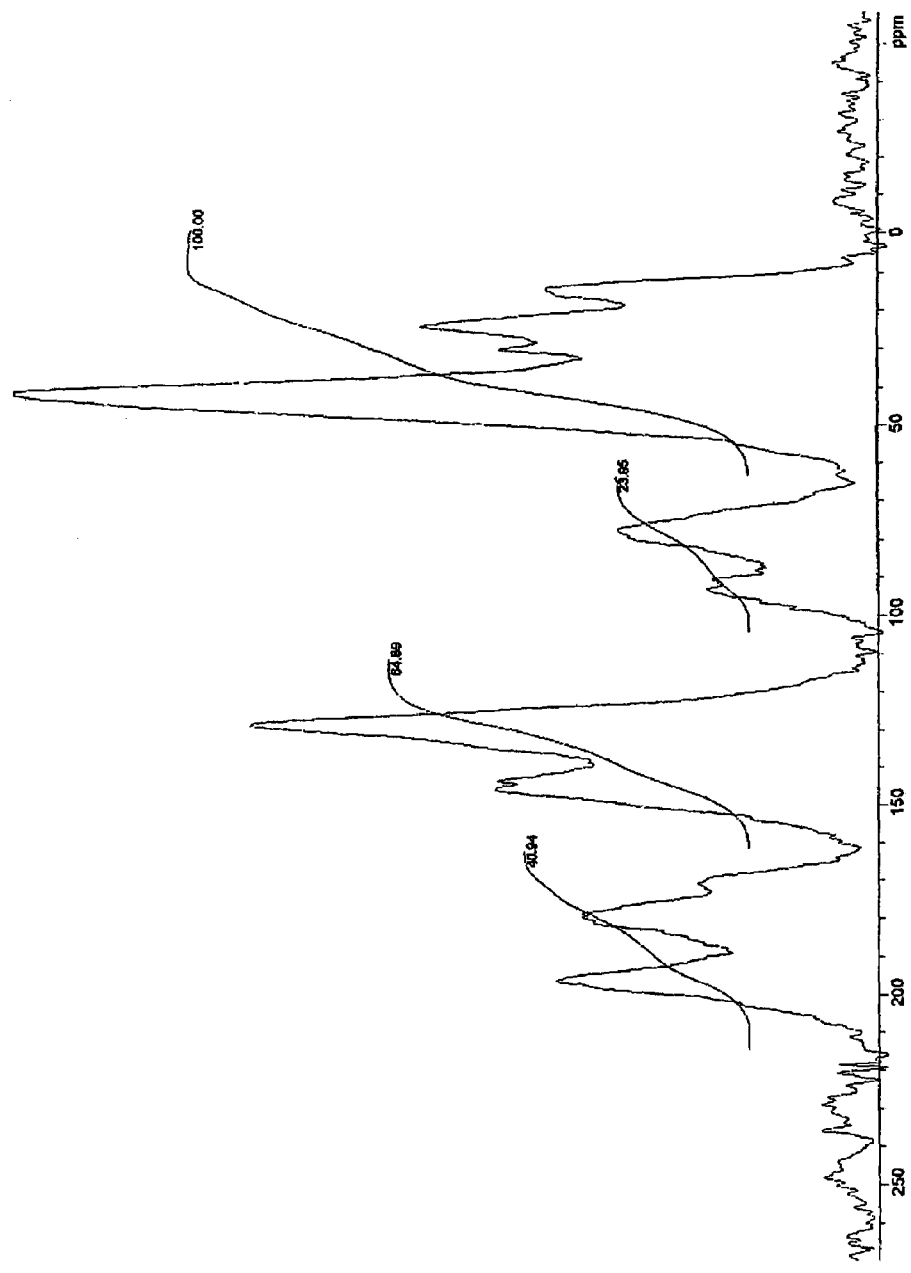
FIG. 3A is a solid-state $^{13}C$ NMR spectrum of a polymeric sorbent of the present invention; the sorbent comprises an acetamide functionality.
Figure 3B:
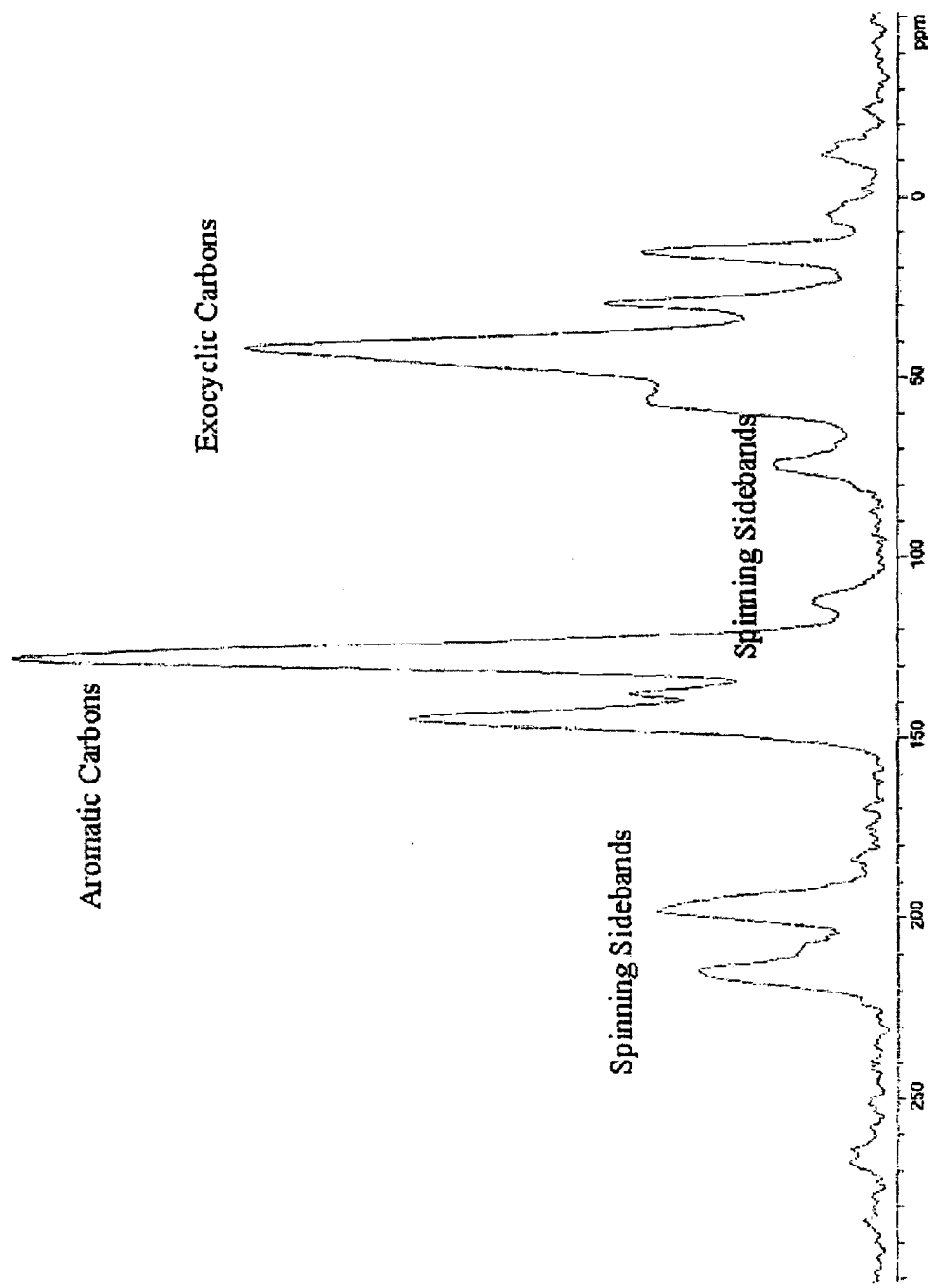
FIG. 3B is solid-state $^{13}C$ NMR of the a [poly(styrene divinylbenzene)] polymer.
Figure 4:
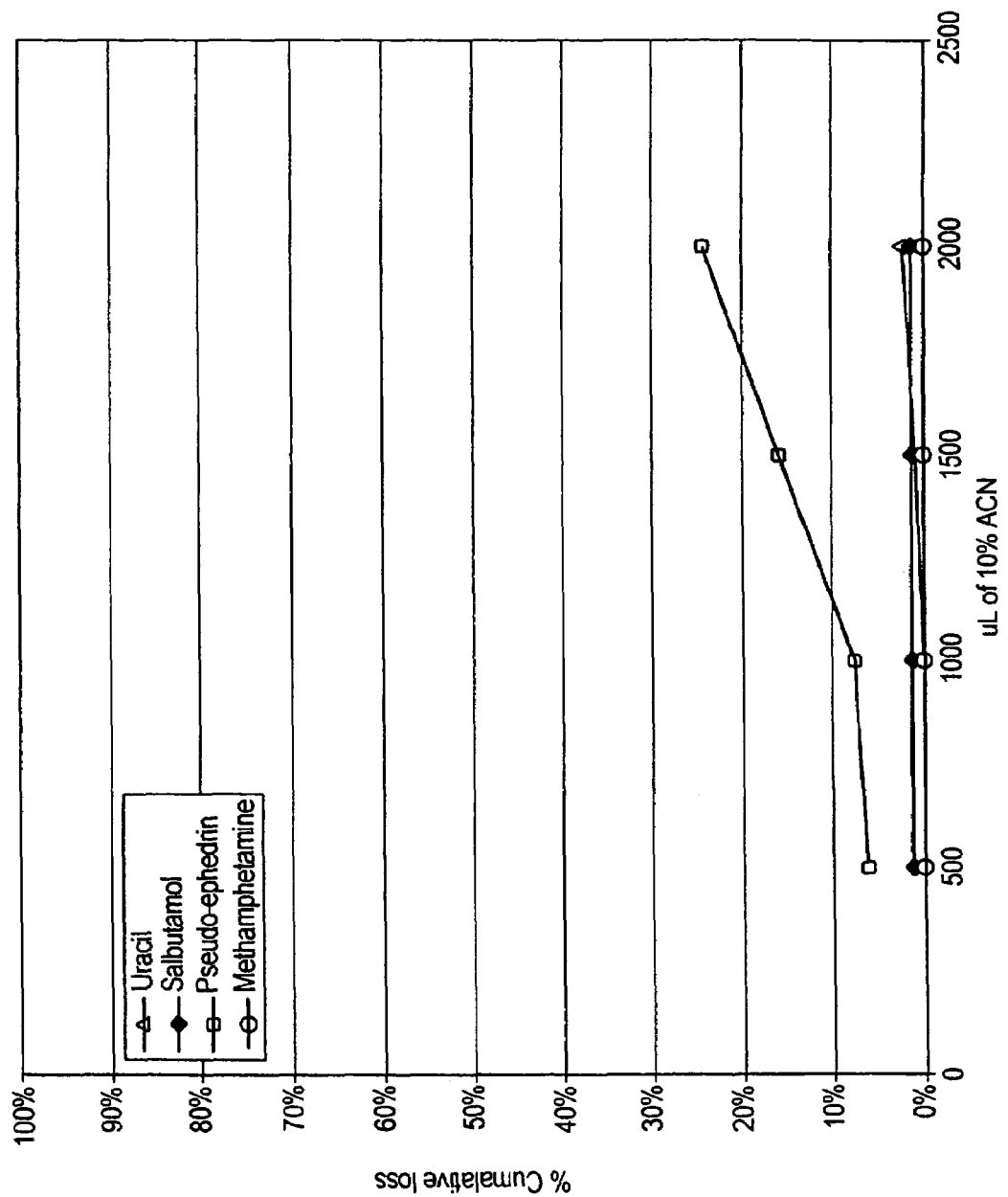
FIG. 4 is a plot depicting the minimal breakthrough of moderately and strongly polar compounds associated with a polymeric sorbent of the present invention during the wash step of an SPE protocol.

Any polymer adapted to form at least one of a dipolar interaction and a hydrophobic interaction can be employed as a polymeric backbone in the present invention. A polymeric backbone can comprise, for example, poly(styrene divinylbenzene), copolymers of styrene or divinylbenzene with functionalized styrenes or heterocycles carrying substituents such as halo, alkoxy, ester or nitro; or copolymers such as (but not restricted to) polystyrene-polyacrylamide and polystyrene-polyacrylates. Thus, a representative, but non-limiting, list of polymers that can be employed as a polymeric backbone in a sorbent of the present invention includes, but is not limited to, poly(styrene divinylbenzene), copolymers comprising styrene or divinylbenzene and methylmethacrylate, halogenated or nitrated or aminated or hydroxylated styrenes, functionalized isocyanurates, urethanes, acrylamides or acrylonitriles and functionalized heterocyclic systems, such as vinyl/allyl pyridines. In one embodiment, a polymeric backbone comprises poly(styrene divinylbenzene), a $^{13}$C NMR spectrum of which is presented in FIG. 3B. It is preferable that the polymeric backbone comprises spherical particles having a characteristic dimension (e.g. a diameter) of between about 20 and about 120 microns in diameter. Although non-spherical or irregular particulate polymers can be employed in the present invention, it is preferable that polymers comprise spherical particles, which are commercially available and can be readily employed in the preparation of a polymeric sorbent of the present invention. Spherical particulate polymers can readily form slurries, exhibit better flow characteristics, can be packed more uniformly and possess greater mechanical stability, which can be desirable in SPE protocols. When a polymeric backbone comprises particles, the particles can be porous and the particles can comprise a pore size of, for example, between about 50 to about 150 angstroms or, for example, between about 50 to about 70 angstroms.

Figure 6:
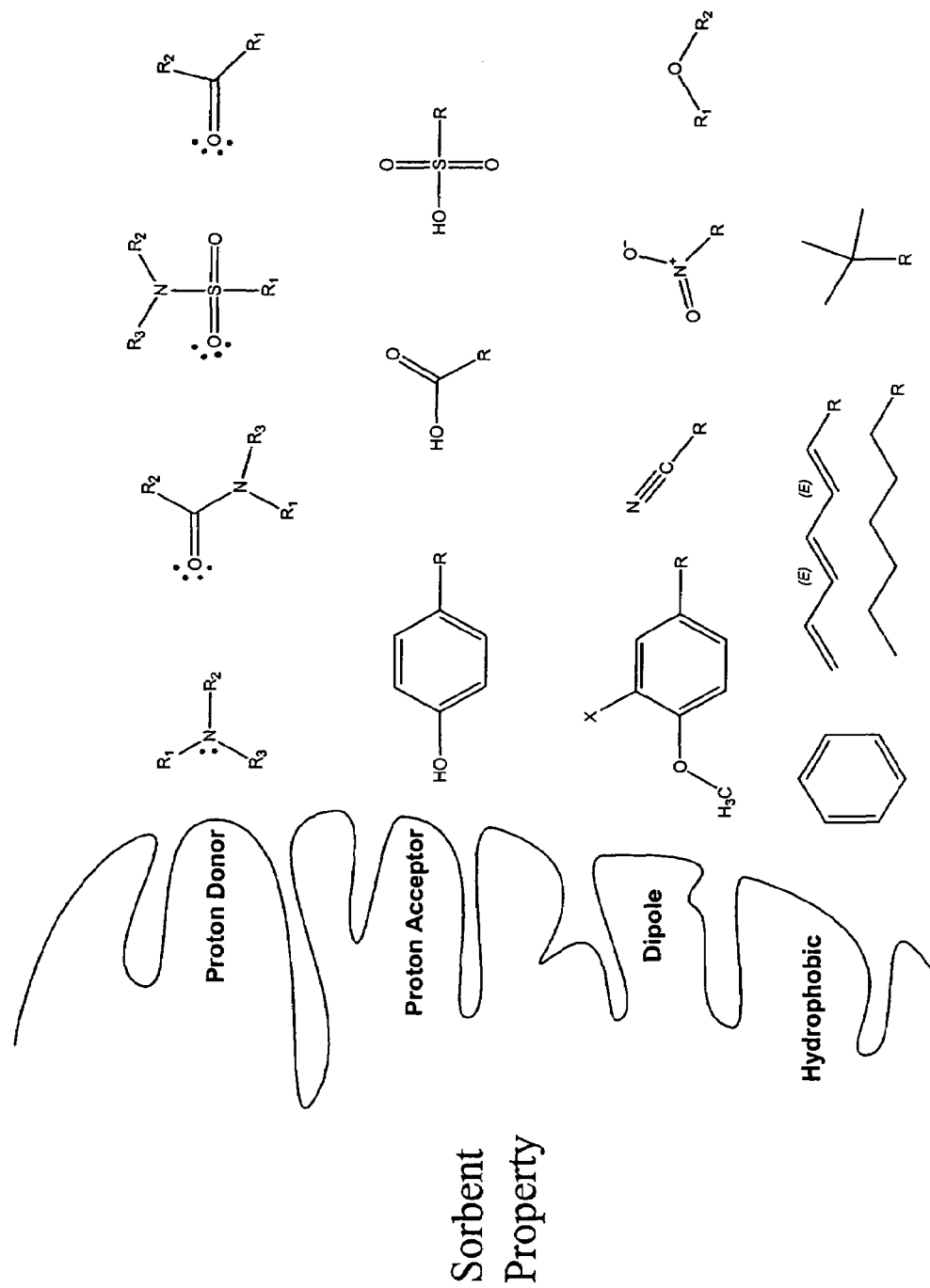
FIG. 6 is a cartoon depicting some polar and hydrophobic interactions that a polymeric sorbent of the present invention can undergo with various analyte functionalities.

A polymeric sorbent of the present invention also comprises an amide functionality associated with the polymeric backbone and adapted to undergo one or more interactions selected from the group consisting of proton accepting, proton donating and dipolar interactions, for example with the functionalities of an analyte. Representative amide functionalities include acetamide, N-alkylamides, N-aryl-amides and N-heteryl amides. Some of the interactions that can occur between an amide functionality and the functional groups of some representative functionalities that are found on an analyte are illustrated in FIG. 6. These interactions can contribute to the retention of different classes of analytes.

An amide functionality can be associated with the polymeric backbone, via a covalent bond, for example, and can be associated at one or more identical positions on the length of a polymeric backbone. Although the configuration of an amide functionality of a polymeric sorbent of the present invention can vary, the nitrogen atom of an amide functionality is preferably associated with a polymeric backbone at one point, a hydrogen atom at another point and a variable organic group at another point as depicted:

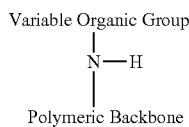

The variable organic group comprises at least one carbonyl, which forms an element of an amide functionality. Although any organic group can form a component of an amide in a sorbent of the present invention, a representative, but non-limiting, list of variable organic groups (which can be associated with a carbonyl) includes methyl, higher alkyl or cycloalkyl, phenyl/alkylphenyl/functionalized phenyl or napthyl or higher polyaromatic ring systems and similarly substituted heterocyclic groups.

A poly(styrene divinylbenzene) polymeric backbone substituted with an acetamide functionality comprises one polymeric sorbent of the present invention. The inclusion of an acetamide functionality in a polymeric sorbent of the present invention affords the sorbent a balance between the retention of polar and hydrophobic drugs under solid phase extraction conditions when compared with other amide derivatives.

In one embodiment, a percentage of nitrogen in a polymeric sorbent of the present invention is between about 3.5% and about 5.0% by mass percent for the retention of both hydrophilic and hydrophobic analytes. In another embodiment, the nitrogen content of a sorbent is between about 4.0% and about 4.5% by mass percent.

In one embodiment of a polymeric sorbent of the present invention, the sorbent can be associated with a support. Some examples of supports include syringe barrel cartridges and multi-well plates (see, e.g., U.S. Pat. No. 6,200,533), although disks, membranes (see, e.g., U.S. Pat. No. 5,738,790), tubes (see, e.g., U.S. Pat. No. 5,137,626) and other supports can also be employed.

A polymeric backbone (and subsequently a polymeric sorbent of the present invention) can, but need not, comprise particles having a characteristic dimension (i.e., diameter) of between about 20 and about 120 microns. In other examples, a polymeric backbone can comprise a pore size of between about 50 to about 150 angstroms, or between about 50 to about 70 angstroms.

V. Preparation of a Polymeric Sorbent of the Present Invention

In one embodiment of the present invention, poly(styrene divinylbenzene) (PS-DVB) was functionalized by the introduction of an amide functionality by a three step synthetic sequence, as shown in FIG. 1 and as described in Laboratory Example 1. The starting polymer, poly(styrene divinylbenzene), is commercially available from several manufacturers as uniform spherical particles (e.g., Polymer Laboratories of Amherst, Mass.; Tosoh Haas of Stuttgart, Germany; and Shodex of Tokyo, Japan).

In the first step of a representative synthetic sequence, PS-DVB can be nitrated with a mixture of nitric and sulfuric acids under optimal conditions to yield a nitrated poly (styrene divinylbenzene). Although the introduction of a nitro moiety into an aromatic nucleus of poly(styrene divinylbenzene) is known in literature, (see, e.g., Philipipides et al., (1993) *Polymer* 34: 3509–3513) the procedures reported are tedious and the conditions employed are drastic. For example, in one prior art method, dimethylformamide was used as a solvent to suspend the polymer and a mixture of fuming nitric acid and sulfuric acid was used and the reaction was initially carried out at 2–5° C. for 3 hours, followed by heating at 60° C. for 6 hours (Philippides et al., (1993) *Polymer* 34: 3509–3513).

In one aspect of the present invention, on the other hand, a simpler and less time-consuming protocol is disclosed. In an example of this aspect of the present invention, a polymeric backbone (poly(styrene divinylbenzene), for example) is suspended in nitric acid and a strong acid (e.g. sulfuric acid) is added over about 1 to about 1.5 hours. The mixture is stirred at room temperature for about 3 hours, thereby forming a nitrated polymeric backbone. Additional discussion of this aspect of the present invention is presented in Laboratory Example 1. Representative amounts of nitric and sulfuric acids used in the nitration reaction are about 25 to about 35 and about 15 to about 20 moles, respectively. During the course of the nitration, stirring can be maintained, and when stirring is maintained a mechanical stirrer operating at a speed of about 100 to about 150 rpm can be employed. Higher stirring speeds might cause breakage of the polymer particles and introduced a high percentage of fines into the product.

In another step of the synthesis of a functionalized poly (styrene divinylbenzene) sorbent of the present invention, the nitrated polymer can be reduced to an amino group by reduction with a catalyst (e.g. stannous chloride) and an acid (e.g. hydrochloric acid), thereby forming an aminated polymeric backbone. The reduction can be performed at room temperature and can be accompanied by stirring. Additional discussion of this aspect of the present invention is presented in Laboratory Example 1. Again, the stirring speed can be regulated to prevent breakage of the polymer spheres.

In another step of the synthesis of a functionalized poly (styrene divinylbenzene) sorbent of the present invention, an aminated polymeric backbone, such as poly(styrene divinylbenzene), is derivatized (acylated, for example) with an acid, an acid chloride or an acid anhydride to yield a desired amide functionalized polymer.

The synthesis of a sorbent of the present invention can optionally comprise additional steps. For example, following the step of contacting an aminated polymeric backbone with an acid, acid chloride or acid anhydride, the resultant sorbent can be recovered by filtration. Filtration through a suitable structure, such as a membrane, can remove the sorbent from solution, making it easy to subsequently treat. The sorbent can then be subjected to additional washes to remove undesired components. Such washes can comprise washing one or more times with an acid, followed washing one or more times with an aqueous solution and washing one or more times with an organic solvent. Cumulatively, these washings can not only remove undesired components that might be associated with the sorbent, but the can also place the sorbent in conditions for either temporary or long term storage until use.

In another aspect of the present invention, several structural analogues were synthesized and screened for their retention characteristics for polar drugs. For example, an aminated poly(styrene divinylbenzene) sorbent of the present invention can be treated with one or more of (a) 4-nitrobenzoyl chloride to yield a 4-nitrobenzoyl amide derivative of the polymer; (b) 4-acetamido benzoylchloride to furnish 4-acetamidobenzoylamide derivative of the polymer; (c) 2-furoyl chloride to provide 2-furoyl amide substituted polymer; and (d) acetic anhydride, in order to generate an acetylamido functionalized poly(styrene divinylbenzene) sorbent of the present invention.

In the preparation of these exemplary compounds, acid chlorides can be employed to introduce the variable organic moiety. In another embodiment, corresponding anhydrides in the presence of a base catalyst can also be employed. In yet another embodiment, a carboxylic acid functionalized variable organic moiety in the presence of a carbodiimide catalyst can also be employed.

V. Properties of a Polymeric Sorbent of the Present Invention

The following sections provide additional detail of the properties of a polymeric sorbent of the present invention, as well as methods of characterizing a polymeric sorbent that was prepared by a method of the present invention.

V.A. Structural Characterization of a Polymeric Sorbent Prepared by a Method of the Present Invention When preparing a polymeric sorbent of the present invention, it can be desirable to confirm the incorporation of a particular functionality (e.g. an amide functionality) into the sorbent, as well as to determine the overall composition and structure of the sorbent. Various spectrophotometric and spectrometric techniques can be employed in this regard. For example, FTIR and solid state $^{13}$C NMR spectroscopy techniques can be employed in the evaluation of a polymeric sorbent of the present invention include. Such techniques are known to those of ordinary skill in the art and, in the context of the present invention, can generally be employed as follows.

A functionalized polymer of the present invention (e.g., an amide functionalized polymer) can be characterized by its Fourier-transform infrared (FTIR) spectrum and its solid state $^{13}$C NMR spectrum. Examples of FTIR and solid state $^{13}$C NMR spectra acquired from a polymeric sorbent are provided in FIG. 2 and FIG. 3A, respectively, for an acetamide functionalized polymeric sorbent.

Figure 2:
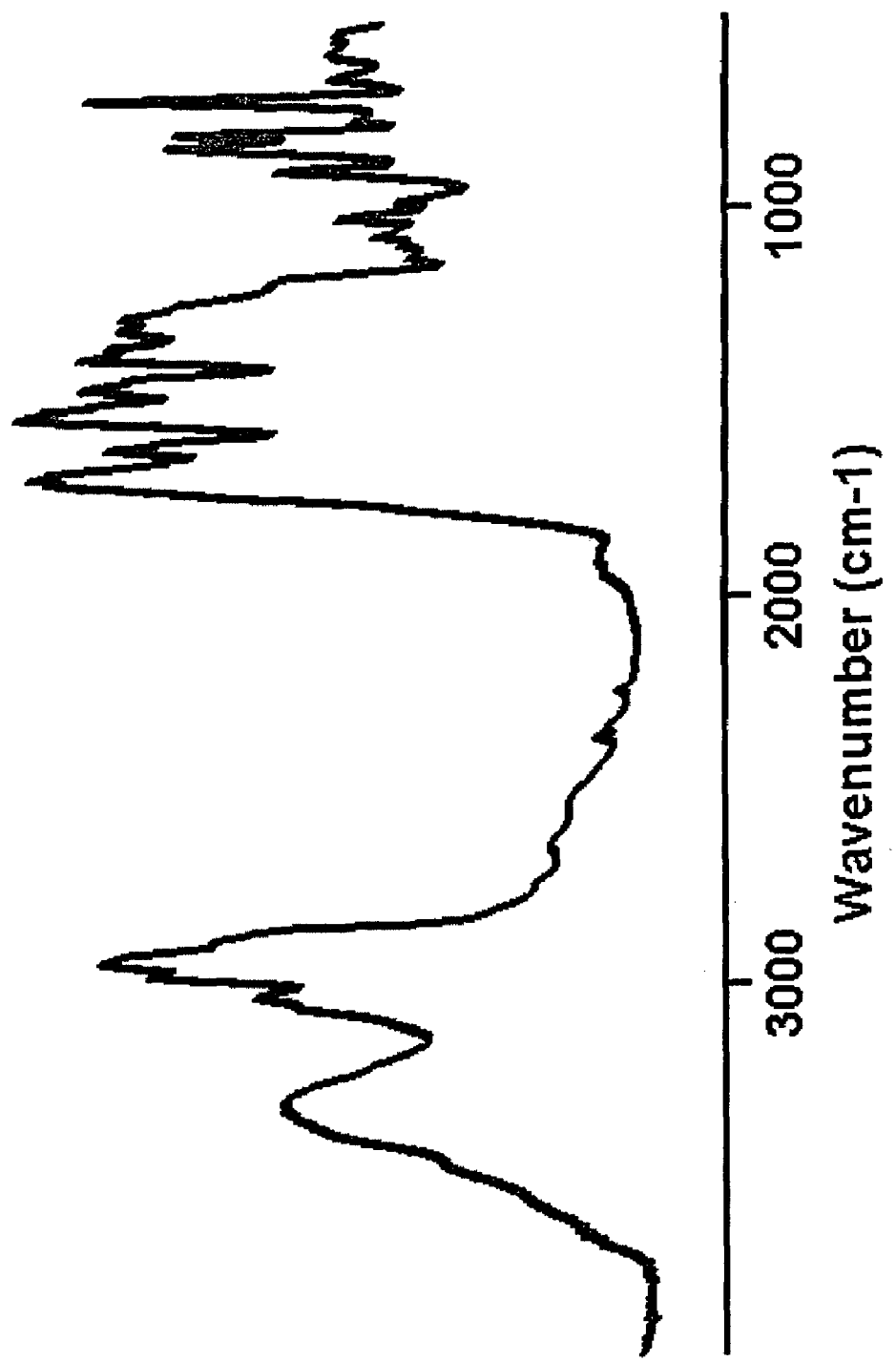
FIG. 2 is an FTIR spectrum of a polymeric sorbent of the present invention; the sorbent comprises an acetamide functionality.

Turning first to FIG. 2, several features of this FTIR spectrum are notable. For example, the peak at about 3000 wavenumbers is characteristic of a methyl C—H stretching vibration and the peak at 3200 cm$^{-1}$ is attributable to an N—H stretching vibration. The envelope at about 1640 wavenumbers is characteristic of the amide carbonyl group stretching vibration, while the bands in the 900–700 wavenumber region can be ascribed to di- and mono-substituted benzene rings. The peaks around 1200 wavenumbers are characteristic of methylene rocking vibrations. Together, these structural features are indicative of the presence of an acetamide functionalized poly(styrene divinylbenzene), an embodiment of a polymeric sorbent of the present invention.

Turning next to FIG. 3A, again several features of this solid state $^{13}$C spectrum serve to characterize the functionalized styrene divinylbenzene polymer. For example, the large peak around 40 ppm, together with the smaller peaks at 29 and 15 ppm are attributable to exocyclic carbons on the aromatic nucleus, while the peaks around 125–140 ppm belong to aromatic ring carbons. The peak around 24 ppm is indicative of the methyl carbon of the acetamide functionality. The downfield peaks at around 150 and 170 ppm are characteristic of carbons situated near the amide nitrogen atom and carbonyl carbons. The peaks found around 70–90 ppm and 180–200 ppm region arise from spinning sidebands, as was proven by their change in position/intensity when the spinner speed is changed. Considered cumulatively, these structural features are indicative of the present of an acetamide funtionalized poly(styrene divinylbenzene), which is an embodiment of a polymeric sorbent of the present invention.

V.B. Solvation Properties of a Polymeric Sorbent of the Present Invention

Several polymeric sorbents documented in the literature are reported to exhibit a high degree of surface hydration (see, e.g., Leon-Gonzalez & Perez-Arribas, (2000) *J. Chromatogr. A* 902: 3–16; Huck & Bonn, (2000) *J. Chromatogr. A* 885: 51–72; U.S. Pat. No. 5,618,438). Some of these polymers comprise a poly(styrene divinylbenzene) backbone and can carry functionalities such as a sulfonic or carboxylic acid moiety, a nitro group, a methyl or phenyl ketone, a hydroxy-methyl group, a quarternary ammonium, or a carboxy-substituted porphyrin moiety. However, these prior art sorbents are not adapted to remain solvated for long periods of time, for example longer than about one hour, while retaining their separative properties.

In one aspect of the present invention, an amide functionality associated with a polymeric backbone (e.g. a poly (styrene divinylbenzene) backbone), which can be an acetamide group, enhances the solvation (e.g. water wettability) of the surface of a polymeric sorbent of the present invention. The enhancement in the solvation is of significance because plasma samples are typically loaded onto SPE sorbents in aqueous solutions and an efficient extraction of a drug contained in the plasma sample will not take place when the sorbent is not wetted (i.e. solvated) or is only partially wetted. Furthermore, after sample loading, the sorbent is typically washed with aqueous solvents, and thorough washing of the drug adsorbed on the sorbent cannot be done without proper wetting of the surface. In addition, configurational changes in the structure/morphology of the sorbent can occur, if the sorbent cannot remain wetted or is not completely wettable.

Figure 7:
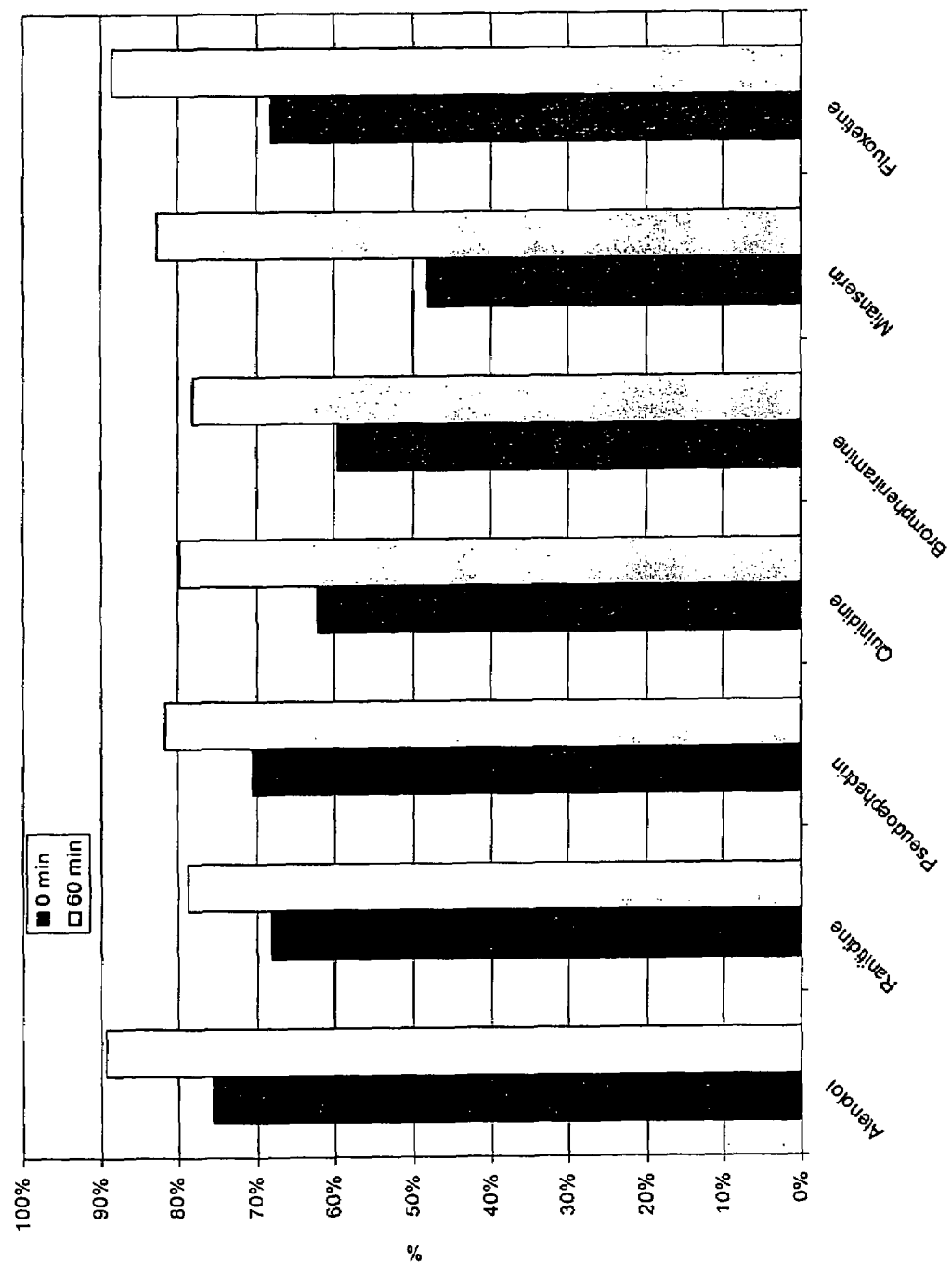
FIG. 7 is a bar graph depicting the effect of post-conditioning drying time on the recovery of seven analytes applied to a polymeric sorbent of the present invention; the analytes were recovered immediately after conditioning the sorbent (black bars) and after a 1 hour drying period following conditioning (white bars).

Even after subjecting a water-wetted polymeric sorbent of the present invention to a vacuum for one hour, the hydration level of the functionalized polymer is not significantly affected. Indeed, after solvation, a polymeric sorbent of the present invention can remain solvated for at least about an hour in the absence of solvent. This property is exhibited in FIG. 7 for a seven component pharmaceutical probe mixture. FIG. 7 demonstrates that the recovery yield of the drugs is significantly enhanced (5 to 30%, maximum observed for the drug mianserin) when the sorbent remains wetted for longer periods after conditioning with water and before the introduction of the sample onto the sorbent. This is due to the fact that a more efficient interaction of the analyte with the sorbent surface takes place when the sorbent reaches equilibrium wettability condition. If the sorbent dries up during standing, drug retention will be significantly altered and washing and elution also become inefficient.

VI. Method of Isolating an Analyte

A polymeric sorbent that is employed in the method comprises a polymeric sorbent of the present invention. As noted hereinabove, the polymeric backbone can comprise any polymer, with the caveat that the polymer be adapted to form at least one of a dipolar interaction and a hydrophobic interaction. A representative, but non-limiting list of polymeric backbone constituents includes, but is not limited to, poly(styrene divinylbenzene), poly(styrene divinylbenzene) functionalized with polar groups such as amide carrying variable organic moieties (e.g. furan or nitrophenyl or ester or ether which can enhance □—□ interactions); a hydroxyphenyl or amidophenyl moiety that can enhance the acidity of the surface for reaction with basic samples; and a basic (e.g. nitrogen containing heterocyclic) moiety that can interact with an acidic sample. A polymeric backbone (and subsequently a polymeric sorbent of the present invention) can, but need not, comprises particles having a characteristic dimension (e.g. a diameter) of between about 20 and about 120 microns. Furthermore, when a polymeric backbone comprises particles, it is the particles can comprise a pore size of, for example, between about 50 to about 150 angstroms, or between about 50 to about 70 angstroms.

Additionally, a polymeric sorbent of the present invention comprises, in one embodiment, an amide functionality adapted to undergo proton accepting and proton donating interactions and associated with the backbone. In other embodiments, the amide functionality can comprise a hydrogen atom and a variable organic group, which itself can comprise a methyl group, making the amide functionality an acetamide group.

In another aspect of the present invention, a method of isolating an analyte from a sample is disclosed. The sample can be derived from any source, although the polymeric sorbent and methods of the present invention are particularly suited for isolating an analyte from biological, environmental and pharmaceutical samples. For example, a sample can comprise biological matrix (e.g., whole blood or plasma or saliva or urine) comprising an analyte of interest (such as a drug). Alternatively, a sample can comprise an environmental sample, such as drinking water or water known or suspected of being polluted. In another example, the analyte of a pharmaceutical sample can comprise a therapeutically-active agent carried by a pharmaceutically-acceptable excipient.

In this embodiment, the method can comprise four general steps: conditioning the sorbent with solvents that enhance surface characteristics, loading the sample contained in an aqueous medium, washing the sample loaded sorbent with an appropriate binary (aqueous organic) solvent and elution with a strong organic solvent.

In this embodiment, the method comprises conditioning the sorbent by washing the sorbent with an organic conditioning solvent followed by water. The sorbent can be associated with a support, such as a column, in which case, the step of conditioning can comprise passing an organic solvent over the column, followed by passing an aqueous solvent over the column. The initial conditioning step can be carried out by treating the sorbent with methanol and then with water (for example about 1 mL each). The methanol swells the sorbent and enhances the effective surface area. The water treatment removes excess methanol and also hydrates the surface. The conditioned surface can then be subjected to vacuum to remove excess solvents; the sorbent remains completely hydrated after this treatment.

Continuing with the embodiment, a sample comprising an analyte can then be contacted with a polymeric sorbent comprising a polymeric backbone adapted to form at least one of a dipolar interaction and a hydrophobic interaction and an amide functionality associated with the backbone and adapted to undergo proton accepting and proton donating interactions to form a sorbent-sample complex. This step, sometimes referred to as sample loading, allows an association of sample, which can comprise an analyte, with a sorbent. The larger the number/nature of interactions of a sample with a sorbent surface, the greater its retention will be. Thus, a sorbent that facilitates a larger number and variety of interactions with a sample will strongly retain the sample.

When a sample comprises a plasma sample, the sample can be introduced as diluted aqueous solutions (at least 1:1 dilution). This practice can be desirable because of the high viscosity of as-obtained plasma samples from animals or humans, which prevents free flow unless diluted to reduce viscosity. The use of organic solvents in this step is preferably avoided, since these solvents can precipitate proteins from the plasma solution and the precipitated proteins can foul the sorbent surface. It can also be desirable that a sample is contacted with a polymeric sorbent under conditions conducive to the formation of an association between an analyte and the polymeric sorbent. At the same time, these conditions are preferably unfavorable for retaining unwanted proteins and other impurities on the sorbent surface. Such conditions can include conducting the contacting at about room temperature and neutral pH.

In a one embodiment of the present invention, a sample is loaded in a 1:1 aqueous solution and an analyte (e.g. a drug) can be present in one nanogram to 10 microgram per milliliter levels. A sample volume of about 100 to about 1000 microliters can be loaded, although volumes of about 400 to about 500 microliters are preferred.

The sorbent-sample complex can then be washed with water, followed by an organic wash solvent. This step can impact the cleanliness of the final eluted sample. In fact, this is one aspect in which the material of the present invention performs at a superior level compared with known SPE sorbents, including polymeric second generation sorbents. In one embodiment, the sample loaded sorbent is washed with water and then with about 10 to about 30% acetonitrile in water (any volume can be employed, although volumes from about 200 to about 1000 microliters are preferred). The water wash removes salts and other water-soluble matrix constituents that might be present in a sample, in addition to proteinaceous matter. The binary aqueous-organic wash can also remove organic impurities including water-insoluble matrix components that can adhere to the sorbent surface. It can be desirable to configure this wash so as not to disrupt the binding of an analyte to the sorbent surface. When many known silica based and polymeric sorbents are employed in a separation, such a binary wash can remove many polar analytes from the sorbent.

Next, an analyte is eluted from the sorbent-sample complex with an eluting solvent. The elution can be performed by passing a volume of an eluting solvent over a sorbent that has been contacted with a sample and with which a sample is associated. Representative eluting solvents include binary solvents comprising an aqueous component and an organic component. Preferably, the organic component comprises at least about 80–90% of the solvent. Representative organic components include, but are not limited to, acetonitrile and methanol. A trailing ion, such as trifluoroacetic acid, can also be employed as a component of an elution solvent and serves to disrupt the polar interactions of polar drugs with the sorbent effectively. In one embodiment of the present invention, a 60:30:10 methanol/acetonitrile/0.1% trifluoroacetic acid is found to afford 90% to almost quantitative recoveries of drugs of a wide range of polarities (see FIG. 8). Eluting solvent volumes of about 400 microliters to about 1000 microliters can be employed, and volumes about 400 to about 500 microlitres are preferred in some situations.

The eluent can be collected and the identity of an adherent analyte ascertained, for example by mass spectrometry, liquid chromatography, gas chromatograpy or a combination of these and other techniques known to those of ordinary skill in the art. When an analyte of interest (e.g. a drug) is present in picogram levels in plasma, the eluting solvent can be evaporated and the residual analyte redissolved (i.e. reconstituted) in about 40 to about 100 microliters of the mobile phase used for LC or LC/MS.

An advantage of the polymeric sorbents and associated methods of the present invention is the ability to pass eluent directly to an instrument(s) for analyte identification. This is not possible with many prior art sorbents, due, in part, to ion suppression effects of prior art sorbents and the inability of these sorbents to retain moderately polar to highly polar analytes. These deficiencies can lead to unwanted components in an eluent, which can significantly complicate analyte identification operations, and poor MS spectra. For example, a sorbent of the present invention can form a component of a system comprising the sorbent and a LC/MS/MS system. Samples can be loaded onto the sorbent, analytes eluted and the eluent stream fed directly into an LC/MS/MS system, HPLC system or any of a range of analytical instruments.

In yet another embodiment of a method of the present invention, the sorbent can be associated with a support or supporting format. A list of representative supports and supporting formats includes syringe barrel cartridges, polymeric fiber membranes, glass fiber membranes and multi-welled plates, although disks and other supports can also be employed. The sorbent can be disposed on the surface of a supporting format, for example on the surface of a multi-welled plate, or the sorbent can be embedded in a supporting format, for example in a polymeric or glass fiber membrane. Thus, by "association" it is generally meant that a sorbent can be in contact with a support or supporting format.

VII. COMPARATIVE EXAMPLES

Figure 8:
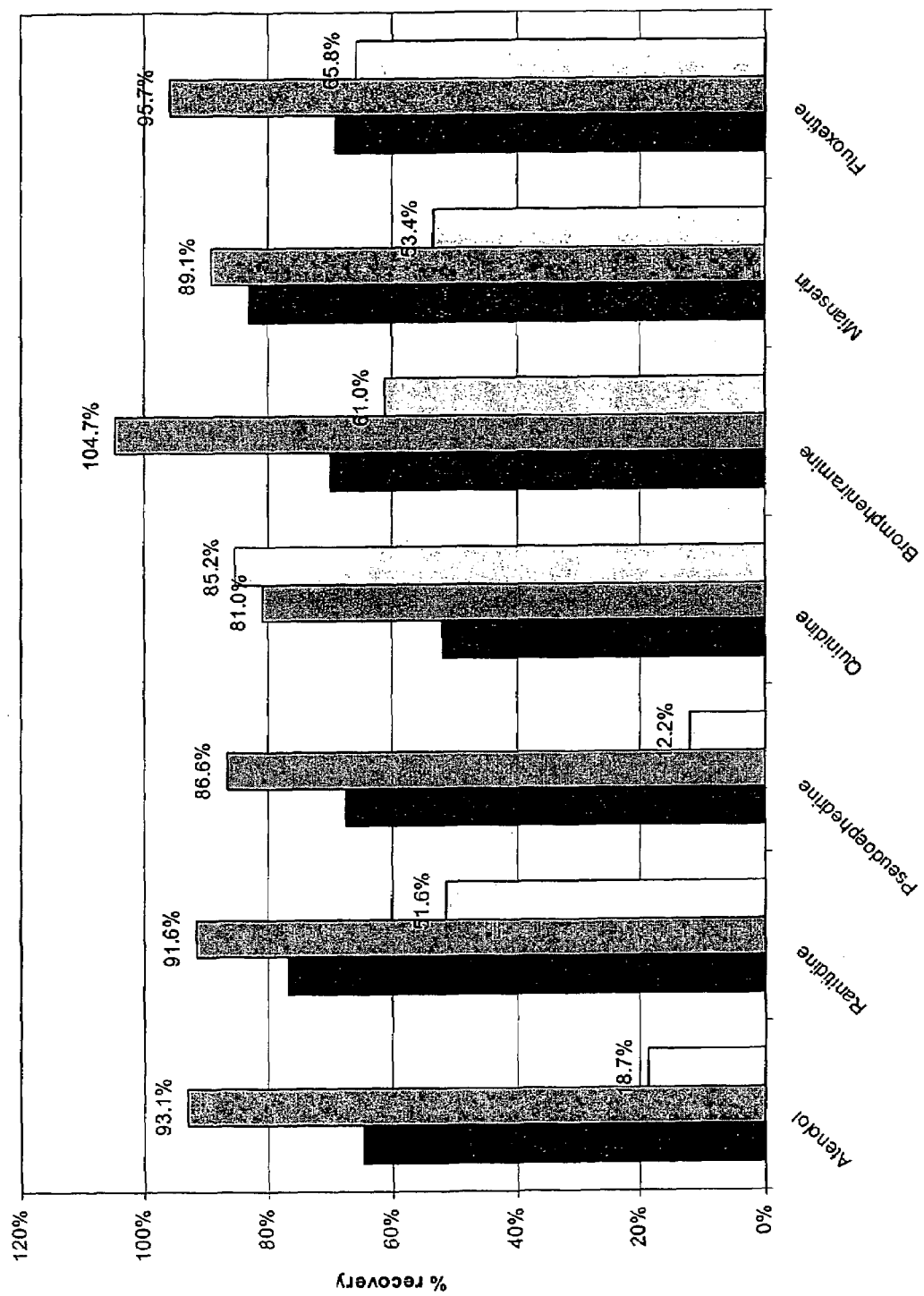
FIG. 8 is a bar graph depicting the recovery of seven analytes from a spiked canine plasma sample which was treated by following a protocol employing a polymeric sorbent of the present invention, as detected by LC/MS/MS. Black bars represent a 400 □l elution from a polymeric sorbent of the present invention; dark gray bars represent a 1 ml elution from a polymeric sorbent of the present invention; light gray bars represent elution from the OASIS® sorbent (Waters Corporation, Milford, Mass.).
Figure 9:
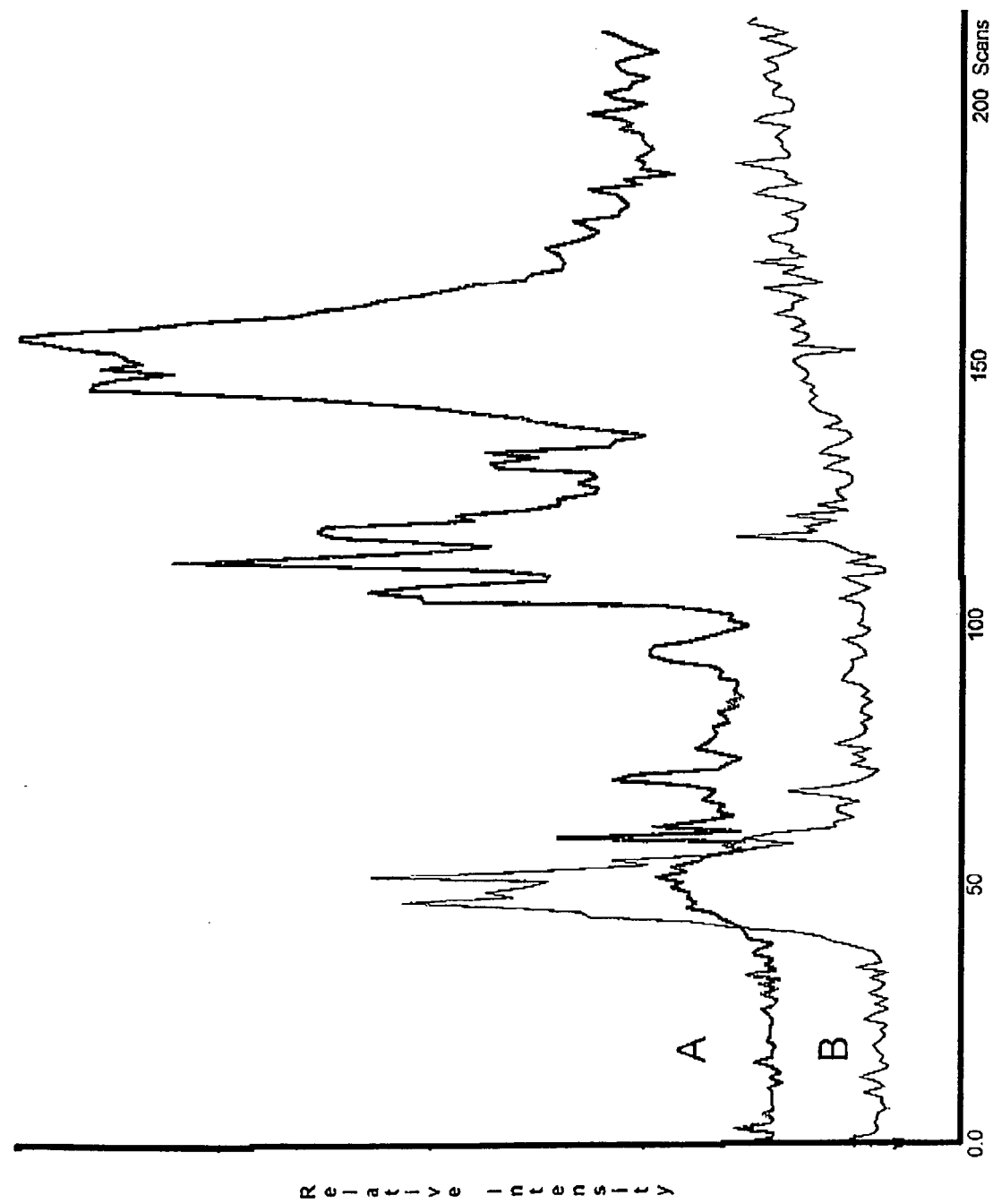
FIG. 9 is a cleanliness check plot in the mass range 500–2200 comparing the purity of a bovine plasma extract isolated by employing a polymeric sorbent of the present invention with the purity of the same sample isolated by employing a commercially available prior art polymeric sorbent in the mass range 500–2200.
Figure 10:
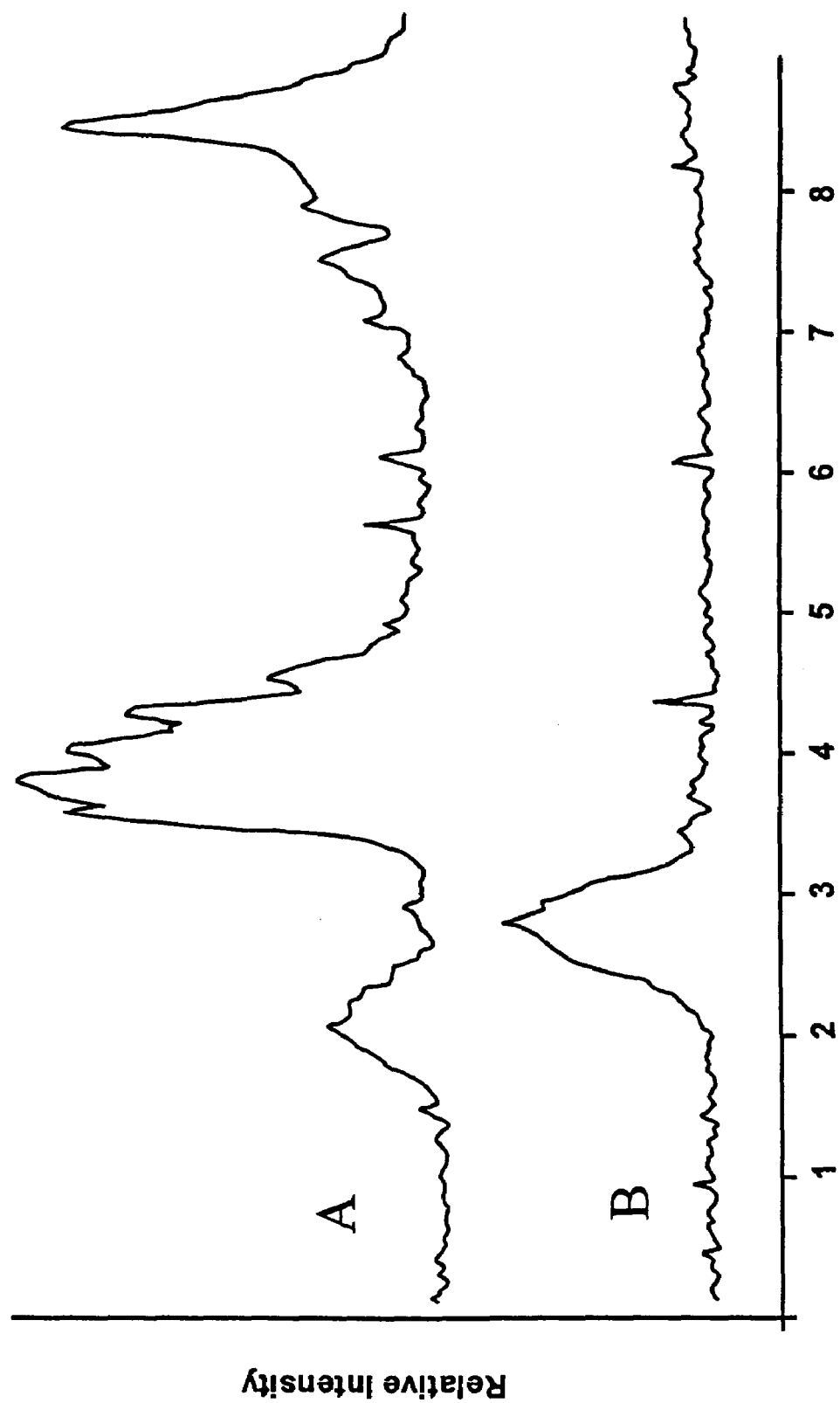
FIG. 10 is a cleanliness indicator plot in the mass range 400–600 comparing the purity of a bovine plasma extract isolated by employing a polymeric sorbent of the present invention with the purity of the same sample isolated by employing a commercially available prior art polymeric sorbent.

In one comparative example, the ability of a polymeric sorbent of the present invention, namely an acetamide functionalized poly(styrene divinylbenzene), to isolate the same combination of eight drugs as mentioned in FIG. 8 from a biological matrix, namely plasma derived from an animal, was investigated. This efficiency was compared with the efficiency of a commercially available prior art polymeric sorbent to perform the same task, namely a divinyl-benzene-N-vinylpyrrolidone resin (commercialized as OASIS® and available from Waters Corporation, Milford, Mass.). FIGS. 9 and 10 summarize the results of this comparative example. These figures show a comparison in the mass ranges 500 to 2200 and 400 to 800, respectively.

Continuing with the comparative example, FIGS. 9 and 10 indicate that the OASIS® resin retains significant proportions of matrix constituents from plasma, which show up as a group of peaks in the mass spectra both in the lower and higher mass regions. For the OASIS® sorbent, the SPE procedure recommended by the manufacturers was followed, while for the polymer of the present invention, the method described in the previous section was employed. The X-axis in both figures represents mass and the Y-axis denotes intensity of each peak as "counts".

Figure 11:
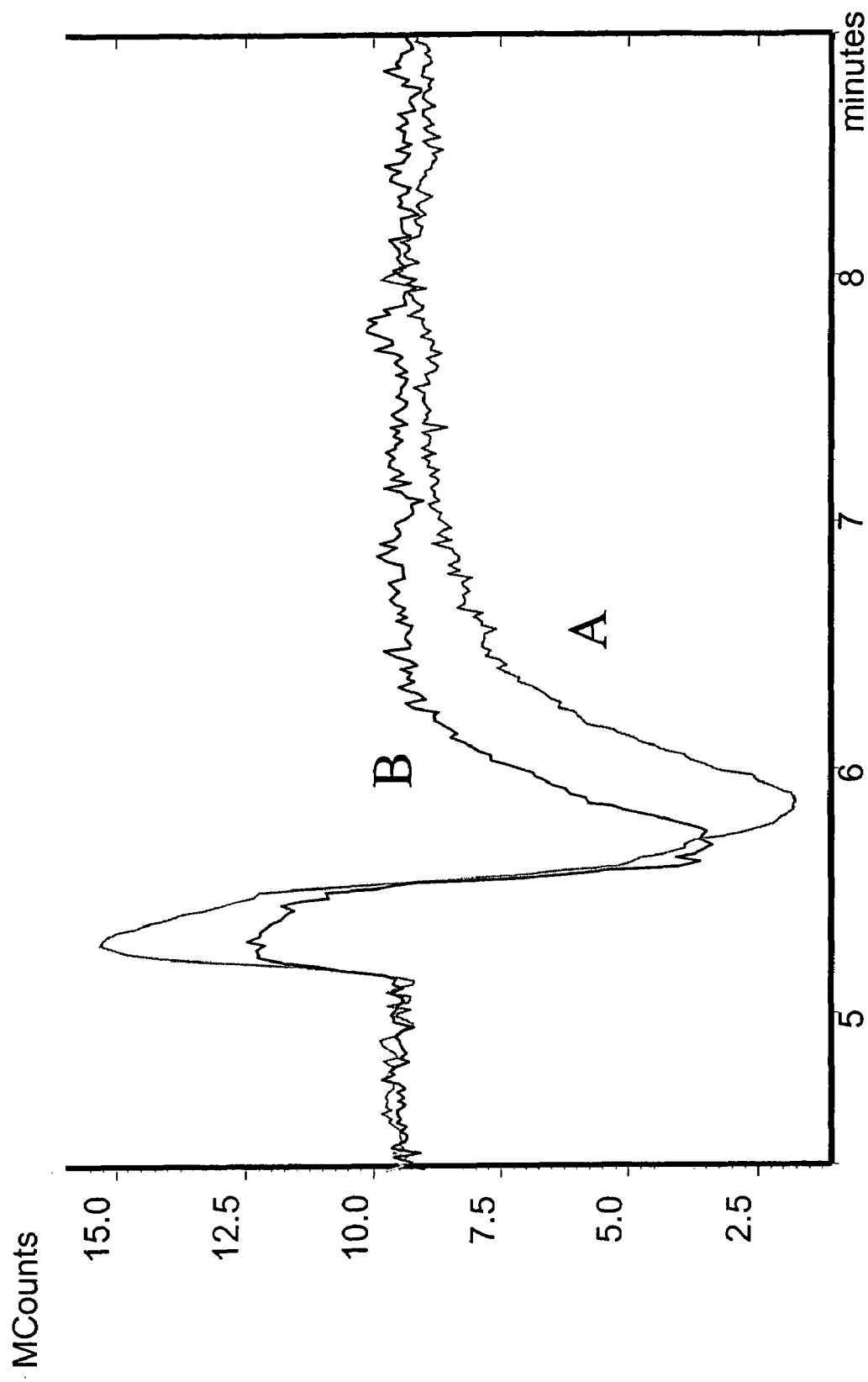
FIG. 11 is a time versus intensity (represented as counts) plot depicting the ion suppression associated with a bovine plasma extract from a polymeric sorbent of the present invention and the ion suppression associated with a commercially available prior art polymeric sorbent.

In another comparative example, the ion suppression of the same polymeric sorbent of the present invention, namely an acetamide functionalized poly(styrene divinylbenzene), was compared with the ion suppression of a commercially available polymeric sorbent, namely the OASIS® sorbent. FIG. 11 presents the results of this comparison. Summarily, FIG. 11 indicates that the polymeric sorbent of the present invention exhibits very low ion suppression under LC/MS/MS analysis employing the ES ionization mode of a mass spectrometric detector.

In one aspect, FIG. 11 indicates that when a polymeric sorbent of the present invention is employed, the minimum part of the curve is much smaller than that achieved when the OASIS® sorbent is employed, and that the curve returns from the minimum point to the original level (starting level) very quickly (in less than 1 min). By way of comparison, when the OASIS® sorbent is employed, it takes more than 10 min (X-axis indicates time in minutes) to do so. This observation indicates that if there are any peaks from analytes (drugs) appearing in this region, they fall under the influence of matrix constituents exhibiting this suppression effect and their intensities are affected.

The data of this comparative example was generated by pumping a constant concentration of a drug (i.e. mianserin) through the LC/MS system at a constant rate and infusing a plasma extract that has been purified by running through the appropriate SPE sorbent into the mobile phase after it had passed through the LC column, and before it enters the mass spectrometer. Since the mobile phase contains a constant level of mianserin, ion suppression due to the infusion (injection) of the plasma extract would result only if there are matrix constituents present in the plasma extract purified by passing through the sorbent.

LABORATORY EXAMPLES

The following Laboratory Examples have been included to illustrate preferred modes of the invention. Certain aspects of the following Laboratory Examples are described in terms of techniques and procedures found or contemplated by the present inventors to work well in the practice of the invention. These Laboratory Examples are exemplified through the use of standard laboratory practices of the inventors. In light of the present disclosure and the general level of skill in the art, those of skill will appreciate that the following Laboratory Examples are intended to be exemplary only and that numerous changes, modifications and alterations can be employed without departing from the spirit and scope of the present invention.

Laboratory Example 1

Preparation of an Acetamide Functionalized Poly(styrene divinylbenzene)

1.A. Nitration

Poly(styrene divinylbenzene) beads (1 mole) was suspended in concentrated nitric acid (30 molar equivalent) and the mixture was mechanically stirred at a low rpm (100–200 rpm) to prevent breakage of the beads. While cooling the mixture in cold water, concentrated sulfuric acid (18 molar equivalent) was added dropwise over a period of 1 to 1.5 hours, continuing the stirring at the same time. The mixture was further stirred at room temperature for three more hours. The reaction mixture was poured into 10–12L of deionized water and after stirring with a polytetrafluoroethylene (commercially available as TEFLON® from DuPont, Wilmington, Del.) tipped rod, the suspension was allowed to stand for 16 hours. The nitrated polymer was recovered by filtering through a sintered glass funnel under vacuum and washed with 2.0M sodium hydroxide initially, followed by 1.0M sodium hydroxide several times and finally with deionized water until the filtrate was no longer basic. The product was then rinsed with acetone and dried under vacuum at 70–80° C.

1.B. Reduction

The nitrated poly(styrene divinylbenzene) was suspended in acetic acid (2.5L) and while mechanically stirring at a low rpm, (100–200 rpm) treated with a solution of stannous chloride (1.25 kg) in 1:1 hydrochloric acid (3L). The mixture was stirred at room temperature for 60 hours. The polymer was recovered by filtration, washed first with deionized water and then 1.0M sodium hydroxide several times till no trace of tin was found in the filtrate. Then the polymer was washed with water until the filtrate is neutral, and then washed with acetone. The product was dried under vacuum at 70–80° C.

1.C. Acetylation

The aminated poly(styrene divinylbenzene) was suspended in a base (triethylamine or pyridine, excess) and with slow mechanical stirring, treated dropwise with acetic anhydride (1.1 mole equivalent to the polymer). The stirring was continued for 3.5 hours. The functionalized polymer was recovered by filtration and washed several times with 0.1 M hydrochloric acid and then with deionized water until the filtrate was neutral. The polymer was washed with methanol several times and then washed with acetone two to three times. Finally, the polymer was dried under vacuum at 70–80° C.

Laboratory Example 2

Solid Phase Extraction of Canine Plasma Sample Spiked with Pharmaceutical Probes The amide functionalized poly(styrene divinylbenzene) sorbent (10 mg) prepared in Laboratory Example 1 was slurry packed into syringe barrel cartridges or a 96 well plate (Ansys/Varian Inc., Palo Alto, Calif.) with water as a slurry solvent. The sorbent was conditioned with 1 mL of methanol, followed by 1 mL of deionized water. A plasma sample spiked with pharmaceutical probes (1:1 diluted, 200 microliters) was then loaded with the application of a gentle vacuum. The cartridge or welled plate was then washed with 1 mL of 10–20% acetonitrile in water under a gentle vacuum. The drugs (analytes) were then eluted with 400–700 microlitres of methanol-water (95:5) or methanol/acetonitrile/water (60:40:10) containing 0.1% of formic or acetic or trifluoroacetic acid. Optionally, the extract could have been concentrated under vacuum and reconstituted in 200 microliters of methanol or acetonitrile, or a mixture of these two solvents, with or without 0.1% of formic or acetic acid. The reconstituted extract was analyzed either by HPLC with UV detection or with LC/MS/MS on a Varian 1200L or PE Sciex API III mass spectrometer detector (Varian Inc., Palo Alto, Calif.).

The recoveries of eight analytes with a wide spectrum of polarities from a canine plasma sample spiked with these pharmaceuticals by solid phase extraction are shown in FIG. 8. The drugs studied comprise of a wide spectrum of polarities, ranging from a log P value of 0.0 to 0.5 for atenolol and ranitidine, to 1.5 for pseudoephedrine, 2.5 for quinidine and 3.0 to 5.0 for brompheneramine, mianserin and fluoxetine. Haloperidol (used as an internal standard) also falls into the hydrophobic drug category. The figure clearly shows that recoveries in the range of 60–70% can be achieved with as small an eluting solvent volume as 400 microliters. Utilizing 1 mL of eluting solvent, the recoveries of all the drugs jumps to about 92–94% for the polar drugs and 81 to 100% for the hydrophobic drugs. In contrast, the recoveries of polar drugs is in the 12 to 19% range when the OASIS® sorbent is employed. These SPE experiments unequivocally demonstrate the universal nature of the polymer of the present invention with equal recoveries/retention for polar, moderately polar and hydrophobic drugs.

Laboratory Example 3

Drying a Sorbent, Followed by SPE

Laboratory Example 3 was conducted in the same manner as described for Laboratory Example 2, with the exception that the conditioned cartridge was dried under gentle vacuum for one hour prior to sample loading. The results of performing an SPE protocol after drying a sorbent of the present invention are presented in FIG. 7.

REFERENCES

Bakerbond SPE Bibliography, JTBaker, Inc, Philipsburg, N.J., 1995

Bonfiglio et al., (1999) *Rapid Commun. Mass Sp.* 13: 1175–1185

Bouvier et al., (1998), *LC.GC (Supplement)*, May 1998, pp S53–S58

Buchmeiser, (2001) *J. Chromatog. A* 918:233–266

Casas et al., (1992) *Chromatographia* 34: 79–82
Cheng et al., (1999) *J. Chromatogr. B* 729: 19–31
Fritz & Macka, (2000) *J. Chromatog. A* 902:137–166
Georga et al., (2001) *J. Chromatogr. B* 759: 209–218
Hennion et al., (1998) *J. Chromatogr. A* 823: 147–161
Hennion, (1999) *J. Chromatogr. A* 856: 3–54
Howard & Meylan, (eds.) 1997 Handbook of Physical Properties of Organic Chemicals, Lewis, Boca Raton, Fla.
Huck & Bonn, (2000) *J. Chromatogr. A* 885: 51–72
*J. Chromatog. A*. (2000) 885: entire issue
King et al., (2000) *J. Am. Soc. Mass Spectr*. 11: 942–950
Kollroser & Schober, (2002) *J. Chromatogr. B* 766: 219–226
Leon-Gonzalez & Perez-Arribas, (2000) *J. Chromatogr. A* 902: 3–16
McDonald & Bouvier, (Eds.), Solid Phase Extraction Applications Guide and Bibliography: A Resource for Sample Preparation Methods Development, Waters Corp., Milford, Mass., 6$^{th}$ ed., 1995
Muller et al., (2002) *J. Chromatogr. B* 773: 47–52
Philippides et al., (1993) *Polymer* 34: 3509–3513
Pichon et al., (1998) *J. Chromatogr. A* 795: 83–92
Sangster, (1989) *J. Phys. Chem. Ref Data* 18(3):1111–1230
Sangster, (1997) Octanol-Water Partition Coefficients: Fundamentals and Physical Chemistry, Wiley, Hoboken N.J.
Simpson (Ed.), (2000) Solid Phase Extraction, Marcel Dekker, New York, N.Y.
Snyder, Kirkland & Glajch, Practical HPLC Method Development, Chapter 4, pp 100–173, Wiley, New York, N.Y. 1997
Thurman & Mills, (1998) Solid Phase Extraction, Wiley, New York, N.Y.
Thurman & Snavely, (2000) Trend Anal. Chem. 19:18–26
Varian Sample Preparation Products, Harbor City, Calif., 1995
Zheng et al., (2002) *J. Pharm. Biomed. Anal*. 28: 279–285
U.S. Pat. No. 5,137,626
U.S. Pat. No. 5,618,438
U.S. Pat. No. 5,738,790
U.S. Pat. No. 5,882,521
U.S. Pat. No. 6,106,721
U.S. Pat. No. 6,200,533

It will be understood that various details of the invention may be changed without departing from the scope of the invention. Furthermore, the foregoing description is for the purpose of illustration only, and not for the purpose of limitation—the invention being defined by the claims.

What is claimed is:

1. A method of isolating an analyte from a sample, the method comprising:
   (a) conditioning the sorbent by washing the sorbent with an organic solvent followed by water;
   (b) contacting a sample comprising an analyte disposed in an aqueous medium with a polymeric sorbent comprising:
      (i) a polymeric backbone adapted to form at least one of a dipolar interaction and a hydrophobic interaction; and
      (ii) an amide functionality associated with the backbone and adapted to undergo proton accepting and proton donating interactions; to form a sorbent-sample complex;
   (c) washing the sorbent-sample complex with a wash solvent; and
   (d) eluting an analyte from the sorbent-sample complex with an eluting solvent, whereby an analyte is isolated from a sample.

2. The method of claim 1, wherein the sample is selected from the group consisting of a biological matrix, an environmental sample, an aqueous pharmaceutical sample and an aqueous nutraceutical sample.

3. The method of claim 1, wherein the polymeric backbone is selected from the group consisting of poly(styrene divinylbenzene), copolymers of styrene, copolymers of divinylbenzene, functionalized styrenes, functionalized heterocycles and combinations thereof.

4. The method of claim 1, wherein the amide functionality is selected from the group consisting of acetamide, N-alkylamides, N-aryl amides and N-heteryl amides.

5. The method of claim 1, wherein the polymeric sorbent comprises between about 3.5% and about 5.0% nitrogen by mass percent.

6. The method of claim 1, wherein the polymeric sorbent comprises particles having a characteristic dimension of between about 20 and about 120 microns.

7. The method of claim 1, wherein the polymeric sorbent remains solvated, after contact with one of a water and an organic solvent, for longer than about one hour.

8. The method of claim 1, wherein the polymeric sorbent is adapted to adsorb strongly polar, moderately polar and nonpolar molecules.

9. The method of claim 1, wherein the eluting solvent comprises an aqueous component and organic component, wherein the organic component comprises greater than about 80% (v/v) of the eluting solvent.

10. The method of claim 1, wherein the polymeric sorbent is associated with a support.

11. The method of claim 10, wherein the support is selected from the group consisting of a cartridge, a polymeric fiber membrane, a glass fiber membrane and a multi-well plate.

12. The method of claim 1, wherein, the conditioning solvent is selected from the group consisting of methanol, water and acetonitrile.

13. The method of claim 1, wherein the wash solvent is selected from the group consisting of water, about 10% to about 30% aqueous acetonitrile and about 10% to about 30% aqueous methanol.

14. A method of isolating an analyte from a sample, the method comprising:
   (a) conditioning the sorbent by washing the sorbent with an organic solvent followed by water;
   (b) contacting a sample comprising an analyte disposed in an aqueous medium with a polymeric sorbent comprising:
      (i) a polymeric backbone adapted to form at least one of a dipolar interaction and a hydrophobic interaction; and
      (ii) an amide functionality associated with the backbone via a covalent bond and adapted to undergo proton accepting and proton donating interactions; to form a sorbent-sample complex;
   (c) washing the sorbent-sample complex with a wash solvent; and
   (d) eluting an analyte from the sorbent-sample complex with an eluting solvent, whereby an analyte is isolated from a sample.

15. A method of isolating an analyte from a sample, the method comprising:
   (a) conditioning the sorbent by washing the sorbent with an organic solvent followed by water;
   (b) contacting a sample comprising an analyte disposed in an aqueous medium with a polymeric sorbent comprising:

(i) a polymeric backbone adapted to form at least one of a dipolar interaction and a hydrophobic interaction; and (ii) an amide functionality associated with the backbone and adapted to undergo proton accepting and proton donating interactions, wherein the nitrogen atom of the amide functionality is associated with the polymeric backbone, a hydrogen atom and a variable organic group comprising a carbonyl, to form a sorbent-sample complex;

(c) washing the sorbent-sanaple complex with a wash solvent; and (d) elating an analyte from the sorbent-sarnple complex wit an elating solvent, whereby an analyte is isolated from a sample.

16. The method of claim 14, wherein the polymeric backbone is selected from the group consisting of poly (styrene divinylbenzene), copolymers of styrene, copolymers of divinylbenzene, functionalized styrenes, functionalized heterocycles and combinations thereof.

17. The method of claim 14, wherein the amide functionality is selected from the group consisting of acetamide, N-allcylamides, N-axyl amides and N-heteryl amides.

18. The method of claim 14, wherein the polymeric sorbent comprises between about 3.5% and about 5.0% nitrogen by mass percent.

19. The method of claim 14, wherein the polymeric sorbent comprises particles having a characteristic dimension of between about 20 and about 120 microns.

20. The method of claim 14, wherein the polymeric sorbent is adapted to adsorb strongly polar, moderately polar and nonpolar molecules.

21. The method of claim 14, wherein the eluting solvent compnses an aqueous component and organic component wherein the organiccomponent comprises greater than about 80% (v/v) of the cluting solvent.

22. The method of claim 14, wherein the polymeric sorbent is associated with a support selected from the group consisting of a cartridge, a polymeric fiber membrane, a glass fiber membrane and a multi-well plate.

23. The method of claim 14, wherein the conditioning solvent is selected from the group consisting of methanol, water and acetonitrile.

24. The method of claim 14, wherein the wash solvent is selected from the group consisting of water, about 10% to about 30% aqueous acetonitrile and about 10% to about 30% aqueous methanol.

* * * * *